US008076535B2

(12) United States Patent  
Jankowski et al.

(10) Patent No.: US 8,076,535 B2
(45) Date of Patent: Dec. 13, 2011

(54) MODULATING PLANT SUGAR LEVELS

(75) Inventors: Boris Jankowski, Newbury Park, CA (US); Kenneth Feldmann, Newbury Park, CA (US); Steven Craig Bobzin, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 11 days.

(21) Appl. No.: 12/256,761

(22) Filed: Oct. 23, 2008

(65) Prior Publication Data
US 2009/0241223 A1 Sep. 24, 2009

Related U.S. Application Data

(63) Continuation of application No. 11/227,976, filed on Sep. 14, 2005, now abandoned.

(60) Provisional application No. 60/610,356, filed on Sep. 14, 2004.

(51) Int. Cl.
C12N 15/82 (2006.01)
C12N 15/00 (2006.01)
C12N 15/09 (2006.01)
C12N 15/29 (2006.01)
A01H 5/00 (2006.01)

(52) U.S. Cl. .............. 800/284; 800/295; 435/320.1; 435/468; 536/23.1; 536/23.2; 536/23.6

(58) Field of Classification Search .............. None
See application file for complete search history.

(56) References Cited

U.S. PATENT DOCUMENTS

| 4,801,540 | A | 1/1989 | Hiatt et al. |
| 4,987,071 | A | 1/1991 | Cech et al. |
| 5,034,323 | A | 7/1991 | Jorgensen et al. |
| 5,204,253 | A | 4/1993 | Sanford et al. |
| 5,231,020 | A | 7/1993 | Jorgensen et al. |
| 5,254,678 | A | 10/1993 | Haseloff et al. |
| 5,283,184 | A | 2/1994 | Jorgensen et al. |
| 5,410,270 | A | 4/1995 | Rybicki et al. |
| 5,445,943 | A | 8/1995 | Hoenes et al. |
| 5,538,880 | A | 7/1996 | Lundquist et al. |
| 5,591,616 | A | 1/1997 | Hiei et al. |
| 5,723,766 | A | 3/1998 | Theologis et al. |
| 5,766,847 | A | 6/1998 | Jackle et al. |
| 5,859,330 | A | 1/1999 | Bestwick et al. |
| 6,004,804 | A | 12/1999 | Kumar et al. |
| 6,010,907 | A | 1/2000 | Kmiec et al. |
| 6,329,571 | B1 | 12/2001 | Hiei |
| 6,423,885 | B1 | 7/2002 | Waterhouse et al. |
| 2004/0031072 | A1 | 2/2004 | La Rosa et al. |
| 2005/0009187 | A1 | 1/2005 | Shinozaki et al. |
| 2005/0246785 | A1 | 11/2005 | Cook et al. |
| 2006/0041952 | A1 | 2/2006 | Cook |
| 2006/0059582 | A1 | 3/2006 | Jankowski et al. |
| 2006/0059585 | A1 | 3/2006 | Jankowski et al. |

FOREIGN PATENT DOCUMENTS

| EP | 1 033 405 | 6/2000 |
| EP | 1033405 | * 9/2000 |
| WO | WO95/35505 | 12/1995 |
| WO | WO 98/07842 | 2/1998 |
| WO | WO 99/32619 | 1/1999 |
| WO | WO99/07865 | 2/1999 |
| WO | WO99/58723 | 11/1999 |
| WO | WO 01/35725 | 5/2001 |
| WO | 01/59136 | 8/2001 |
| WO | WO 01/75164 | 10/2001 |
| WO | WO 02/15675 | 2/2002 |
| WO | WO 02/46449 | 6/2002 |
| WO | WO 03/013227 | 2/2003 |
| WO | WO 03044190 | 5/2003 |
| WO | WO 2004/035798 | 4/2004 |
| WO | WO 2006/005023 | 1/2006 |

OTHER PUBLICATIONS

U.S. Appl. No. 60/121,700, Feb. 25, 1999, Bouckaert et al.
GenBank Accession No. CAA16567 dated Nov. 14, 2006, 2 pages.
GenBank Accession No. CAA19798 dated Nov. 14, 2006, 2 pages.
GenBank Accession No. CAB79237 dated Nov. 14, 2006, 2 pages.
GenBank Accession No. AAN72006 dated Nov. 19, 2002, 2 pages.
GenBank Accession No. AAP21371 dated Apr. 25, 2003, 2 pages.
GenBank Accession No. Q9LTM2 dated Nov. 28, 2006, 2 pages.
GenBank Accession No. Q9LTM1 dated Nov. 28, 2006, 3 pages.
GenBank Accession No. BAB02441 dated Feb. 14, 2004, 2 pages.
GenBank Accession No. BAB02440 dated Feb. 14, 2004, 2 pages.
GenBank Accession No. AAK25981 dated Sep. 18, 2002, 2 pages.
GenBank Accession No. AAK64138 dated Sep. 18, 2002, 2 pages.
GenBank Accession No. NP 004553, dated Feb. 11, 2007.
GenBank Accession No. NP 194013 dated Jun. 9, 2006, 2 pages.
GenBank Accession No. NP 974594 dated Jun. 9, 2006, 2 pages.
GenBank Accession No. NP 189251 dated Jun. 9, 2006, 2 pages.
GenBank Accession No. NP 189250 dated Jun. 9, 2006, 2 pages.
Ahn et al., "Homoeologous relationship of rice, wheat and maize chromosomes" *Molecular and General Genetics*, 241:483-90 (1993).
Albert et al., "Site-specific integration of DNA into wild-type and mutant lox site placed in the plant genome" *The Plant Journal*, 7:649 (1995).
Alonso-Blanco et al. (Methods in Molecular Biology, vol. 82, "*Arabidopsis* Protocols", pp. 137-146, J.M. Martinez-Zapater and J. Salinas, eds., c. 1998 by *Humana Press*, Totowa, NJ).
*Arabidopsis* P450 Gene Family. Retrieved from the Internet: URL:http://www.arabidopsis.org/info/genefamily/p450.html, dated Jul. 29, 2004.
*Arabidopsis thaliana* —MTC11.11 / At3g26200. Retrieved from the Internet: 2000 URL:http://www.tigr.org/tigr-scripts/euk_manatee/shared/ORF_infopage.cgi?db=athl&orf=At3g.
Armaleo, et al., "Biolistic nuclear transformation of *Saccharomyces cerevisiae* and other fungi" *Current Genetics*, 17:97 (1990).
AtMYB23 Myb transcription factor target down-regulation; Jul. 6, 2004. Retrieved from the Internet: URL:http://www.ncbi.nlm.nih.gov/projects/geo/gds/gds_browse.cgi?gds=694, document undated.
Ausubel et al. (Current Protocols in Molecular Biology, *Greene Publishing*, New York (1992)).

(Continued)

Primary Examiner — Brent T Page
(74) Attorney, Agent, or Firm — Fish & Richardson P.C.

(57) ABSTRACT

This document provides methods and materials related to plants having modulated (e.g., increased) levels of sugars (e.g., glucose, fructose, and/or sucrose). For example, this document provides plants having increased sugar levels as well as methods and materials for making plants and plant products having increased sugar levels.

23 Claims, 10 Drawing Sheets

OTHER PUBLICATIONS

Azpiroz-Leehan et al., "T-DNA insertion mutagenesis in *Arabidopsis*: going back and forth" *Trends in Genetics*, 13:152 (1997).

Baerson, et al., "Developmental regulation of an acyl carrier protein gene promoter in vegetative and reproductive tissues" *Plant Molecular Biology*, 22(2), pp. 255-267 (1993).

Bateman, et al., "Pfam 3.1: 1313 multiple alignments and profile HMMs match the majority of proteins" *Nucleic Acids Research*, vol. 27, (1999), pp. 260-262.

Bechtold, et al., "In planta *Agrobacterium* mediated gene transfer by infiltration of adult *Arabidopsis thaliana* plants" *C.R. Acad. Sci. Paris*, 316, pp. 1194-1199 (1993).

Bonner et al., "Reduction in the Rate of DNA reassociation by Sequence Divergence" *J. Mol. Biol.*, 81:123 (1973).

Bradshaw et al., "A new vector for recombination-based cloning of large DNA fragments from yeast artificial chromosomes" *Nucl. Acids. Res.*, 23:4850-4856 (1995).

Brummell, et al., Inverted repeat of a heterologous 3'-untranslated region for high-efficiency, high-throughput gene silencing; *The Plant Journal*, 33, pp. 793-800 (2003).

Burke et al., "Cloning of large segments of exogenous DNA into yeast by means of artificial chromosome vectors" *Science*, 236:806-812 (1987).

Burr ("Mapping Genes with Recombinant Inbreds", pp. 249-254. In Freeling, M. and V. Walbot (Ed.), The Maize Handbook, c. 1994 by Springer-Verlag New York, Inc.: New York, NY, USA; Berlin Germany.

Burr et al., "Gene mapping with recombinant inbreds in maize" *Genetics*, 118:519 (1998).

Bustos, et al., "Regulation of β-Glucuronidase Expression in Transgenic Tobacco Plants by an A/T-Rich, cis-Acting Sequence Found Upstream of a French Bean β-Phaseolin Gene" *The Plant Cell*, vol. 1, pp. 839-853 (1989).

Carels et al., "Compositional properties of homologous coding sequences from plants" *J. Mol. Evol.*, 46:45 (1998).

Cerdan, et al., A 146 bp fragment of the tobacco Lhcb1 *2 promoter confers very-low-fluence, low-fluence and high-irradiance responses of phytochrome to a minimal CaMV 35S promoter, Plant *Molecular Biology*, 33, pp. 245-255 (1997).

Chen, et al., "Functional analysis of regulatory elements in a plant embryo-specific gene" *Proc. Natl. Acad. Sci. USA*, vol. 83, pp. 8560-8564 (1986).

Christou, "Strategies for variety-independent genetic transformation of important cereals, legumes and woody species utilizing particle bombardment" *Euphytica*, 85(1-3):13-27, (1995).

Conkling, et al., "Isolation of transcriptionally regulated root-specific genes from tobacco" *Plant Physiol.*, 93:1203-1211 (1990).

De Feyter, et al., "Expressing Ribozymes in Plants; Methods in Molecular Biology" vol. 74, Chapter 43 (Edited by Turner, P.C., *Humana Press Inc.*, Totowa, NJ) 1997.

De Martinis et al., "Silencing gene expression of the ethylene-forming enzyme results in a reversible inhibition of ovule development in transgenic tobacco plants" *Plant Cell*, 11:1061 (1999).

deVicente and Tanksley "QTL analysis of transgressive segregation in an interspecific tomato cross" *Genetics*, 134:585 (1993).

Escudero, et al., "T-DNA transfer in meristematic cells of maize provided with intracellular *Agrobacterium*" *The Plant Journal*, 10(2), pp. 355-560 (1996).

Evans et al., Protoplasts Isolation and Culture in "Handbook of Plant Cell Culture," pp. 124 176, *MacMillan Publishing Company*, New York, 1983.

Fejes, et al., "A 268 bp upstream sequence mediates the circadian clock-regulated transcription of the wheat Cab-1 gene in transgenic plants" *Plant Molecular Biology*, 15, pp. 921-932 (1990).

Fennoy et al. "Synonymous codon usage in *Zea mays* L. nuclear genes is varied by levels of C and G-ending codons" *Nucleic Acids Research*, 21(23):5294 (1993).

Frischauf et al., "Lambda replacement vectors carrying polylinker sequences" *J. Mol. Biol.*, 170:827-842 (1983).

Fromm et al. "Expression of genes transferred into monocot and dicot plant cells by electroporation" *Proc. Natl. Acad. Sci. USA*, 82:5824 (1985).

Fromm, et al., "An octopine synthase enhancer element directs tissue-specific expression and binds ASF-1, a factor from tobacco nuclear extracts" *The Plant Cell*, 1:977-984 (1989).

Gardiner et al., "Development of a core FRLP map in maize using an immortalized $F_2$ population" *Genetics*, 134:917 (1993).

Gene References into Function (GeneRIF). Retrieved from the Internet: URL: http://www.ncbi.nlm.nih.gov/entrez/query.fcgi?db-gene&cmd=Retrieve&dopt=Graphics&1, document printed Jun. 6, 2005.

Ghosh et al. "Transgenic indica rice (*Oryza sativa* L.) plants obtained by direct gene transfer to protoplasts" *J. Biotechnol.*, 32:1-10 (1994).

Gleave, "A versatile binary vector system with a T-DNA organizational structure conducive to efficient integration of cloned DNA into the plant genome" *Plant Mol. Biol.*, 20:1203 (1992).

Golovkin et al., "An SC35-like protein and a novel serine/arginine-rich protein interact with *Arabidopsis* U1-70K protein" *J. Biol. Chem.* 274:36428 (1999).

Gould et al., "Transformation of *Zea mays* L. Using *Agrobacterium tummefaciens* and the shoot apex" *Plant Physiology*, 95:426 (1991).

Graves and Goldman, "The transformation of *Zea mays* seedling with *Agrobacterium tumefaciens*" *Plant Mol. Biol.*, 7:34 (1986).

Hamilton, "A binary-BAC system for plant transformation with high-molecular-weight DNA" *Gene*, 200:107-116 (1997).

Hamilton et al., "Antisense gene that inhibits synthesis of the hormone ethylene in transgenic plants" *Nature*, 346:284-287 (1990).

Hamilton et al., "Stable transfer of intact high molecular weight DNA into plant chromosomes" *Proc. Natl. Acad. Sci. USA*, 93:9975-9979 (1996).

Herrera-Estrella et al., "Chimeric genes as dominant selectable markers in plant cells" *EMBO J.*, 2:987 (1983).

Hong, et al., "Promoter sequences from two different *Brassica napus* tapetal oleosin-like genes direct tapetal expression of β-glucuronidase in transgenic *Brassica* plants" *Plant Molecular Biology*, 34(3), pp. 549-555 (1997).

Hosoyama et al. "Oryzacystatin exogenously introduced into protoplasts and regeneration of transgenic rice" *Biosci. Biotechnol. Biochem.*, 58:1500 (1994).

Hu et al., "*Escherichia coli* one- and two-hybrid systems for the analysis and identification of protein-protein interactions" *Methods*, 20:80 (2000).

Huynh et al., In: Glover NM (ed) DNA Cloning: A practical Approach, vol. 1 *Oxford: IRL Press* (1985).

Hyrup, et al., "Peptide Nucleic Acids (PNA): Synthesis, Properties and Potential Applications" *Bioorganic & Medicinal Chemistry*, 4(1), pp. 5-23 (1996).

Ichimura, et al., "Isolation of ATMEKK1 (a MAP Kinase Kinase Kinase)—interacting proteins and analysis of a MAP Kinase cascade in *Arabidopsis*" *Biochem. Biomes. Res. Comm.* 253:532 (1998).

International Search Report from International Application No. PCT/US05/32680.

Ishida, et al., "High efficiency transformation of maize (*Zea mays* L.) mediated by *Agrobacterium tumefaciens*" *Nature Biotechnology*, vol. 14, pp. 745-750 (1996).

Keegstra and Cline, "Protein import and routing systems of chloroplasts" *The Plant Cell*, 11:557-570 (1999).

Keller and Manak (DNA Probes, 2nd Ed. pp. 1-25, c. 1993 by *Stockton Press*, New York, NY).

Klee et al. "*Agrobacterium*-mediated plant transformation and its further applications to plant biology" *Ann. Rev. of Plant Phys.*, 38:467 (1987).

Klein et al. "High-velocity microprojectiles for delivering nucleic acids into living cells" *Nature*, 327:773 (1987).

Kohler and Milstein "Continuous cultures of fused cells secreting antibody of predefined specificity" *Nature*, 256: 495 (1975).

Komari et al., "Vectors carrying two separate T-DNAs for co-transformation of higher plants mediated by *Agrobacterium tumefaciens* and segregation of transformants free from selection markers" *Plant J.*, 10:165 (1996).

Lam, et al., "Site-specific mutations alter in vitro factor binding and change promoter expression pattern in transgenic plants" *Pro. Natl. Acad. Sci. USA*, vol. 86, pp. 7890-7894 (1989).
Liljegren, "Interactions among APETALA1, LEAFY, and TERMINAL FLOWER1 specify meristem fate" *Plant Cell*, 11:1007 (1999).
Luan, et al., "A rice cab gene promoter contains separate cis-Acting elements that regulate expression in dicot and monocot plants" *The Plant Cell*, 4:971-981 (1992).
Lubberstedt, et al., "Promoters from genes for plastid proteins possess regions with different sensitivities toward red and blue light" *Plant Physiol.*, 104:997-1006 (1994).
Luo et al., "Mapping sequence specific DNA-protein interactions: A versatile, quantitative method and its application to transcription factor XF1" *J. Mol. Biol.* 266:479 (1997).
Mariani et al., "A chimaeric ribonuclease-inhibitor gene restores fertility to male sterile plants" *Nature*, 357: 384-387 (1992).
Marra et al., "High throughput fingerprint analysis of large-insert clones" *Genomic Research*, 7:1072-1084 (1997).
Martinez et al., "Creation of ecdysone receptor chimeras in plants for controlled regulation of gene expression" *Mol. Gen. Genet.*, 261:546 (1999).
Marty, "Plant Vacuoles" *The Plant Cell*, 11:587-599 (1999).
Matsui, et al., NimbleGen 60mer *Arabidopsis* array; National Institute of Advanced Industrial Science and Technology (AIST); Jul. 7, 2004. Retrieved from the Internet: URL:http://www.ncbi.nlm.nih.gov/projects/geo/query/acc.cgi?acc=GPL1323.
Matsuoka, et al., "Tissue-specific light-regulated expression directed by the promoter of a C4 gene, maize pyruvate,orthophosphate dikinase, in a C3 plant, rice" *Proc. Natl. Acad. Sci. USA*, vol. 90, pp. 9586-9590 (1993).
Matteucci et al. "Synthesis of Deoxyoligonucleotides on a polymer support" *J. Am. Chem. Soc.*, 103:3185 (1981).
May, et al., "Generation of Transgenic Banana (*Musa acuminate*) Plants via *Agrobacterium*-Mediated Transformation" *Bio/Technology*, vol. 13, pp. 486-492 (1995).
McAlister-Henn et al., "Application of the yeast two-hybrid system" *Methods*, 19:330 (1999).
McCormac et al., "A flexible series of binary vectors for *agrobacterium*-mediated plant transformation" *Mol. Biotechnol.*, 8:199 (1997).
Michaels et al., "Flowering Locus C encodes a novel MADS domain protein that acts as a repressor of flowering" *The Plant Cell*, 11:949 (1999).
Mizutani, et al., "Cytochrome p450 superfamily in *Arabidopsis thaliana*: isolation of cDNAs, Differential Expression, and RFLP mapping of multiple cytochromes P450" *Plant Molecular Biology* 37, pp. 39-52 (1998).
Müller et al., "High meiotic stability of a foreign gene introduced into tobacco by *Agrobacterium*-mediated transformation" *Mol. Gen. Genet.*, 207:171 (1987).
Napoli et al., "Introduction of a chimeric chalcone synthase gene into petunia results in reversible co-suppression of homologous genes in trans." *The Plant Cell*, 2:279 (1990).
Needleman and Wunsch "A general method applicable to the search for similarities in the amino acid sequence of two proteins" *J. Mol. Biol.*, 48:443 (1970).
Oeller et al., "Reversible inhibition of tomato fruit senescence by antisense RNA" *Science*, 254:437-439 (1991).
Pan, et al., "GAL4 transcription factor is not a "zinc finger" but forms a Zn(II)2Cys6 binuclear cluster" *Proc. Natl. Acad. Sci. USA*, vol. 87, pp. 2077-2081 (1990).
Panaud et al., "Frequency of microsatellite sequences in rice (*Oryza sative* L.)" *Genome*, 38:1170 (1995).
Paquette, et al., "Intron-Exon Organization and Phylogeny in a Large Superfamily, the Paralogous Cytochrome P450 Genes of *Arabidopsis thaliana*" *DNA and Cell Biology*, vol. 19, No. 5, pp. 307-317 (2000).
Paszkowski et al. "Direct gene transfer to plants" *EMBO J.*, 3:2717 (1984).
Pearson and Lipman "Improved tools for biological sequence comparison" *Proc. Natl. Acad. Sci. USA*, 85: 2444 (1988).
Perriman, et al., "Effective ribozyme delivery in plant cells" *Proc. Natl. Acad. Sci. USA*, vol. 92(13), pp. 6175-6179 (1995).

Refseth et al., "Hybridization capture of microsatellites directly from genomic DNA" *Electrophoresis*, 18:1519 (1997).
Riggs, et al., "Cotyledon Nuclear Proteins Bind to DNA Fragments Harboring Regulatory Elements of Phytohemagglutinin Genes" *The Plant Cell*, vol. 1(6), pp. 609-621 (1989).
Rivera, et al., "Genomic evidence for two functionality distinct gene classes" *Proc. Natl. Acad. Sci. USA*, vol. 95, pp. 6239-6244 (1998).
Salomon et al., "Genetic identification of functions of TR-DNA transcripts in octopine crown galls" *EMBO J.*, 3:141 (1984).
Sambrook et al. (Molecular Cloning, a Laboratory Manual, 2nd ed., c. 1989 by *Cold Spring Harbor Laboratory Press*, Cold Spring Harbor, NY).
Sato, et al., "Structural analysis of *Arabidopsis thaliana* chromosome 3. I. Sequence features of the regions of 4,504,864 bp covered by sixty P1 and TAC clones" *DNA Res.* 7 (2), 131-135 (2000).
Schwarz et al., "The basic region of myogenin cooperates with two transcription activation domains to induce muscle-specific transcription" *Mol. Cell. Biol.*, 12:266 (1992).
Senior et al., "Simple sequence repeat markers developed from Maize sequences found in the Genbank database: Map construction" *Crop Science*, 36:1676 (1996).
Sheehy et al., "Reduction of polygalacturonase activity in tomato fruit by antisense RNA" *Proc. Nat. Acad. Sci. USA*, 85:8805 (1988).
Shizuya et al., "Cloning and stable maintenance of 300-kilobase-pair fragments of human DNA in *Escherichia coli* using an F-factor-based vector" *Proc. Natl. Acad. Sci. USA*, 89:8794-8797 (1992).
Slocombe, et al., "Temporal and tissue-specific regulation of a *Brassica napus* stearoyl-acyl carrier protein desaturase gene" *Plant Physiol.*, 104(4):167-176 (1994).
Smith and Waterman, "Comparison of Biosequences" *Advances in Applied Mathematics.*, 2:482 (1981).
Sonnhammer, et al., "Pfam: multiple sequence alignments and HMM-profiles of protein domains" *Nucleic Acids Research*, vol. 26, (1998), pp. 320-322.
Sonnhammer, et al., "Pfam: A Comprehensive Database of Protein Domain Families Based on Seed Alignments" *Proteins: Structure, Function, and Genetics*, vol. 28 (1997), pp. 405-420.
Sternberg et al., "Bacteriophage P1 cloning system for the isolation, amplification, and recovery of DNA fragments as large as 100 kilobase pairs" *Proc. Natl. Acad. Sci. USA*, 87(1):103-7 (1990).
Summerton and Weller, Morpholino Antisense Oligomers: Design, Preparation, and Properties, *Antisense & Nucleic Acid Drug Development.*, 7, pp. 187-195 (1997).
Tanksley and McCouch, "Seed banks and molecular maps: Unlocking genetic potential from the wild" *Science*, 277:1063 (1997).
Taramino et al., "Simple sequence repeats for germplasm analysis and mapping in maize" *Genome*, 39:277 (1996).
Tian, et al., "How Well is Enzyme Function Conserved as a Function of Pairwise Sequence Identity?" *J. Mol. Biol.*, 333, pp. 863-882 (2003).
Tijessen, "Hybridization with Nucleic Acid Probes" in Laboratory Techniques in Biochemistry and Molecular Biology, P.C. vand der Vliet, ed., c. 1993 by *Elsevier*, Amsterdam.
Truernit, et al., "The promoter of the *Arabidopsis thaliana* SUC2 sucrose-H+ symporter gene directs expression of β-glucuronidase to the phloem: Evidence for phloem loading and unloading by SUC2" *Planta*, 196, pp. 564-570 (1995).
Urdea et al. "Chemical synthesis of a gene for human epidermal growth factor urogastrone and its expression in yeast" *Proc. Natl. Acad. Sci. USA*, 80:7461 (1983).
Van der Krol et al., "Flavonoid genes in petunia: Addition of a limited number of gene copies my lead to a suppression of gene expression" *The Plant Cell*, 2:291 (1990).
Van Eenennaam, et al., "Elevation of seed χ-tocopherol levels using plant-based transcription factors targeted to an endogenous locus" *Metabolic Engineering*, 6, pp. 101-108 (2004).
Vaucheret et al., "Transgene-induced gene silencing in plants" *The Plant Journal*, 16:651-659 (1998).
Venkateswarlu et al., "Evidence for T-DNA mediated gene targeting to tobacco chloroplasts" *Biotechnology*, 9:1103 (1991).
Vergunst et al., "Site-specific integration of *Agrobacterium* T-DNA in *Arabidopsis thaliana* mediated by Cre recombinase" *Nucleic Acids Res.*, 26:2729 (1998).

Vergunst et al., "Cre/lox-mediated site-specific integration of *Agrobacterium* T-DNA in *Arabidopsis thaliana* by transient expression of cre" *Plant Mol. Biol.*, 38:393 (1998).

Vitale and Denecke, "The endoplasmic reticulum-gateway of the secretory pathway" *The Plant Cell*, 11:615-628 (1999).

Walden et al., "A novel 205-kilodalton testis-specific serine/threonine protein kinase associated with microtubules of the spermatid manchette" *Mol. Cell. Biol.*, 1:175-194 (1990).

Weising et al., "Foreign genes in plants: transfer, structure, expression, and applications" *Ann. Rev. Genet.*, 22:421 (1988).

Werck-Reichhart, et al., "Cytochromes P450; The Arabidopsis Book" (2002). Retrieved from the Internet: URL:http://www.arabidopsis.org/servlets/TairObject?type=publication&id=501681274.

Wilson, et al., "Assessing Annotation Transfer for Genomics: Quantifying the Relations between Protein Sequence, Structure and Function through Traditional and Probabilistic Scores" *J. Mol. Biol.* 297, pp. 233-249, (2000).

Xu, et al., "Microarray-based analysis of gene expression in very large gene families: the cytochrome P450 gene superfamily of *Arabidopsis thaliana*" *Gene*, 272, pp. 61-74 (2001).

Yamamoto, et al., "The Promoter of a Pine Photosynthetic Gene Allows Expression of a β-Glucuronidase Reporter Gene in Transgenic Rice Plants in a Light-Independent but Tissue Specific Manner" *Plant Cell Physiol.*, 35(5), pp. 773-778 (1994).

Yanagisawa, S., "The Dof family of plant transcription factors" *Trends in Plant Science*, vol. 7, No. 12; pp. 555-560 (2002).

Yanagisawa, et al., "Metabolic engineering with Dof1 transcription factor in plants: Improved nitrogen assimilation and growth under low-nitrogen conditions" *PNAS*, vol. 101, No. 20, pp. 7833-7838 (2004).

Zhang, et al., "Synthetic Zinc Finger Transcription Factor Action at an Endogenous Chromosomal Site" *The Journal of Biological Chemistry*, vol. 275, No. 43, pp. 33850-33860 (2000).

Zheng, et al., "SPK1 is an essential S-phase-specific gene of *Saccharomyces cerevisiae* that encodes a nuclear serine/threonine/tyrosine kinase" *Mol. Cell Biol.*, 13-5829-5842 (1993).

Alexandrov et al., "Features of *Arabidopsis* genees and genome discovered using full-length cDNAs" *Plant Molecular Biology*, 60(1):69-85 (2006).

Broun et al. "Catlytic plasticity of fatty acid modification enzymes underlying chemical diversity of plant lipids" *Science*, 282(13):1315-1317 (1998).

Doerks et al. "Protein annotation: Detective work for function prediction" *TIG*, 14(6):248-250 (1998).

Galweiler et al. "Techincal advance: the DNA-binding activity of ga14 is inhibited by methylation of the ga14 binding site in plant chromatin" *Plant Journal*, 23(1):143-157 (2000).

Haas et al. "Full-length messenger RNA sequences greatly improve genome annotation" *Genome Biology*, 3:1-12 (2002).

Lazar et al. "Transforming growth factor a: Mutation of aspartic acid 47 and leucine 48 in different biological activities" *Molecular & Cell Biology*, 8(3):1247-1252 (1988).

SCORE search results details, for SEQ ID No. 2, pp. 1-3, printed on Oct. 6, 2006.

* cited by examiner

Figure 1 aatataaccacctcacatttttttcatcactccttaaagatgacaacagcagaaaaaacttcaaacttggatctcatacgccaacacctctttggt
gaaaacatcatctcagactcctcctcctttgtctccaatctccatcatcatcctgtgaaacttgaaccccccctcatcaccagaatttgatttcacct
catatatcttagataacaacacaagcagcaacttcttcacattccttgaaggctatgatttggtggcagacatgaagtttgtaattgattcagaca
acaccaccaccatggtgatcccttcaaaggaggttataaagaaatgcaatattaattctcctgaagaacaaccaatggtgtcatcatcatcaga
agagaagccaacaatgaaaaagtcagaacattatgatgaggcaaagcgttataggggagttaggagaaggccatgggggaaatttgctgc
tgaaatccgtgaccctacaaggaaagggacaagggttactagaagatcttcgtcgtccaatgcttccttgcccgcaagcccattgcgataatt
agttacagcattggaaaagaataagcaatgttctcgattgcacttcattccctttcaaaagaaggcaatttgggggcaagcttcttttttgttcata
gccgaattagtcacaacatttattcattggatgcaacattgggactcttggaaagtgttggc

Figure 2

Met Thr Thr Ala Glu Lys Thr Ser Asn Leu Asp Leu Ile Arg Gln His Leu Phe Gly Glu Asn Ile Ile
Ser Asp Ser Ser Ser Phe Val Ser Asn Leu His His His Pro Val Lys Leu Glu Pro Pro Ser Ser Pro
Glu Phe Asp Phe Thr Ser Tyr Ile Leu Asp Asn Asn Thr Ser Ser Asn Phe Phe Thr Phe Leu Glu
Gly Tyr Asp Leu Val Ala Asp Met Lys Phe Val Ile Asp Ser Asp Asn Thr Thr Thr Met Val Ile
Pro Ser Lys Glu Val Ile Lys Lys Cys Asn Ile Asn Ser Pro Glu Glu Gln Pro Met Val Ser Ser Ser
Ser Glu Glu Lys Pro Thr Met Lys Lys Ser Glu His Tyr Asp Glu Ala Lys Arg Tyr Arg Gly Val
Arg Arg Arg Pro Trp Gly Lys Phe Ala Ala Glu Ile Arg Asp Pro Thr Arg Lys Gly Thr Arg Val
Thr Arg Arg Ser Ser Ser Ser Asn Ala Ser Leu Pro Ala Ser Pro Leu Arg

Figure 3 ctctccaaatttcttcttcttctccggcgaagaaatcgaaaagtcattaccctaagagtcccagagtcgtcagaaggaacagcttttgaaatgg
acggtgtcacataccaaagattcccaacggtgaagatccgtgagcttaaagatgactacgccaagttcgagcttcgtgaaaccgacgtttca
atggccaacgctctccgtcgcgtaatgatctccgaagtccccaccatggcaatccatctcgtcaaaatcgaggttaattcctctgttctcaacg
acgagttcattgctcaacgacttcgtctcatccctctcactagcgagcgtgctatgagcatgcggttctgtcaagattgtgaagattgtaacgga
gatgaacattgcgagttctgctctgttgagtttccccttagtgctaagtgtgttactgaccaaaccctagatgttactagtagggatctctacagt
gctgatcctactgttactcctgttgatttcactagtaactcatctacttctgattcaagcgagcacaagggaattatcattgcgaaactacgcagg
ggacaagagttgaagcttaaagcattagcgaggaaaggaattgggaaagatcatgcgaaatggtctcctgcagctactgttacgtatatgtat
gagcctgacattattatcaatgaagagatgatgaacactttgacagatgaggaaaaaattgacttgattgagagcagtcctaccaaagtgtttg
gcattaccggacaggttaatttcgatgttctgtaagaataacatctatacaagtttatagctttgagacttcaatatgattgtactactttataggcta
ccatgctttgaaatatatgtatgtgatgtggtgtatgaattttctttaagtgtttagtgcgtttagccc

Figure 4

Met Asp Gly Val Thr Tyr Gln Arg Phe Pro Thr Val Lys Ile Arg Glu Leu Lys Asp Asp Tyr Ala Lys Phe Glu Leu Arg Glu Thr Asp Val Ser Met Ala Asn Ala Leu Arg Arg Val Met Ile Ser Glu Val Pro Thr Met Ala Ile His Leu Val Lys Ile Glu Val Asn Ser Ser Val Leu Asn Asp Glu Phe Ile Ala Gln Arg Leu Arg Leu Ile Pro Leu Thr Ser Glu Arg Ala Met Ser Met Arg Phe Cys Gln Asp Cys Glu Asp Cys Asn Gly Asp Glu His Cys Glu Phe Cys Ser Val Glu Phe Pro Leu Ser Ala Lys Cys Val Thr Asp Gln Thr Leu Asp Val Thr Ser Arg Asp Leu Tyr Ser Ala Asp Pro Thr Val Thr Pro Val Asp Phe Thr Ser Asn Ser Ser Thr Ser Asp Ser Ser Glu His Lys Gly Ile Ile Ile Ala Lys Leu Arg Arg Gly Gln Glu Leu Lys Leu Lys Ala Leu Ala Arg Lys Gly Ile Gly Lys Asp His Ala Lys Trp Ser Pro Ala Ala Thr Val Thr Tyr Met Tyr Glu Pro Asp Ile Ile Ile Asn Glu Glu Met Met Asn Thr Leu Thr Asp Glu Glu Lys Ile Asp Leu Ile Glu Ser Ser Pro Thr Lys Val Phe Gly Ile Thr Gly Gln Val Asn Phe Asp Val Leu

| | | | | | | |
|---|---|---|---|---|---|---|
| SEQ-ID-NO-5 | TVTFMYEPDI | RINQELMETL | TLEEKQSWVE | SSPTKVFDID | PVTQQVTVD | 250 |
| SEQ-ID-NO-10 | TVTFMYEPDI | RINQELMETL | TLEEKQSWVE | SSPTKVFDID | -------- | 240 |
| SEQ-ID-NO-6 | TVTFMYEPDI | RINEELMETL | IVEERLSLIE | SSPTKVFELD | SA-NQVVKN | 247 |
| SEQ-ID-NO-11 | TVTFMYEPDI | RINEELMETL | IVEERLSLIE | SSPTKVFELD | -------- | 238 |
| SEQ-ID-NO-7 | TVTFMYEPEI | RINEELMETL | LEEKRNLVE | SSPTKVFNID | PNTQQVVED | 249 |
| SEQ-ID-NO-12 | TVTFMYEPEI | RINEELMETL | LEEKRNLVE | SSPTKVFNID | -------- | 239 |
| SEQ-ID-NO-4 | TVTFMYEPEI | RINEDLMETL | LEEKREMVD | SSPTRVFEID | PVIQQVMVD | 234 |
| SEQ-ID-NO-9 | TVTYMYEPEI | HINEELMETL | LEEKREMVD | SSPTRVFEID | PV------- | 226 |
| LEAD-SEQ-ID-NO-2 | TVTFMYEPDI | -NEEMMNLL | TDEEKIDLIE | SSPTKVFGIT | GQVNFDVL | 232 |
| SEQ-ID-NO-3 | TVTFMYEPDI | NEDMMDTL | SDEEKIDLIE | SSPTKVFGMD | PVTRQVVVD | 234 |
| SEQ-ID-NO-8 | TVTFMYEPDI | NEDMMDTL | SDEEKIDLIE | SSPTKVFGMD | PV------- | 226 |

Consensus: TVTFMYEPDI  RINEELMETL  TLEEKR-LVE  SSPTKVF-ID  P------V-  250

| | | | | | | |
|---|---|---|---|---|---|---|
| SEQ-ID-NO-5 | PEAYTYDDEV | IKKAEAMGKP | GLVEINAKED | SFVFTVETTG | AITAYELIMN | 300 |
| SEQ-ID-NO-10 | -------- | -------- | -------- | -------- | -------- | 240 |
| SEQ-ID-NO-6 | AEAYTYDDEV | IKHAEAIGKP | GLVEITAKED | SFVFTVETTG | AITAYELIMN | 297 |
| SEQ-ID-NO-11 | -------- | -------- | -------- | -------- | -------- | 238 |
| SEQ-ID-NO-7 | AEAYTYDDEV | IKKADAMGKP | GLIEINAKED | SFIFTVETTG | AITAYELIMN | 299 |
| SEQ-ID-NO-12 | -------- | -------- | -------- | -------- | -------- | 239 |
| SEQ-ID-NO-4 | AEAYTYDDEV | LKKAEAMGKP | GLIEIARQD | SFIFTVESTG | AVKASQLVLN | 284 |
| SEQ-ID-NO-9 | -------- | -------- | -------- | -------- | -------- | 226 |
| LEAD-SEQ-ID-NO-2 | -------- | -------- | -------- | -------- | -------- | 232 |
| SEQ-ID-NO-3 | PEAYTYDEEV | IKKAEAMGKP | GLIEISPKDD | SFIFTVESTG | AVKASQLVLN | 284 |
| SEQ-ID-NO-8 | -------- | -------- | -------- | -------- | -------- | 226 |

Consensus: 300

| | | | | |
|---|---|---|---|---|
| SEQ ID NO-5 | AITVLRQKLD | AVRLQDD---- | -DGDLGELGA | HLIGG | 331 |
| SEQ ID NO-10 | AITVLRQKLD | AVRLQDD---- | ---------- | ------ | 240 |
| SEQ ID NO-6 | AITVLRQKLD | AVRLQDD---- | -DGDLGELGA | HLGGP | 328 |
| SEQ ID NO-11 | AITVLRQKLD | AVRLQDD---- | ---------- | ------ | 238 |
| SEQ ID NO-7 | AITVLRQKLD | AVRLQDD---- | -DADLGELGA | HLVGG | 330 |
| SEQ ID NO-12 | AITVLRQKLD | AVRLQDD---- | ---------- | ------ | 239 |
| SEQ ID NO-4 | AIEILKQKLD | AVRLSEDTVE | ADDQFGELGA | HMRGG | 319 |
| SEQ ID NO-9 | ---------- | ---------- | ---------- | ------ | 226 |
| LEAD SEQ ID NO-2 | AIDLLKQKLD | AVRLSDDTVE | ADDQFGELGA | HMRGG | 232 |
| SEQ ID NO-3 | ---------- | ---------- | ---------- | ------ | 319 |
| SEQ ID NO-8 | ---------- | ---------- | ---------- | ------ | 226 |
| Consensus | | | | | 335 |

FIGURE 6D

MODULATING PLANT SUGAR LEVELS

CROSS-REFERENCE TO RELATED APPLICATIONS

This Application is a continuation of and claims priority under 35 U.S.C. §120 to U.S. application Ser. No. 11/227,976, filed Sep. 14, 2005, now abandoned which claims priority under 35 U.S.C. §119 to U.S. Provisional Application No. 60/610,356, filed Sep. 14, 2004, incorporated herein by reference in its entirety.

TECHNICAL FIELD

This document provides methods and materials related to plants having modulated (e.g., increased) levels of sugars (e.g., glucose, fructose, and/or sucrose). For example, this document provides plants having increased sugar levels as well as methods and materials for making plants and plant products having increased sugar levels.

BACKGROUND

A sugar is a carbohydrate that is sweet to taste. Sugars are used in food and drink as a source of sweetness and energy and are important in biochemistry. Sucrose, also called "table sugar," is a white crystalline solid. Sucrose is a disaccharide composed of two monosaccharides, glucose and fructose, joined together by a 1→2-α,β-glycosidic bond. Sucrose is commercially extracted from either sugar cane or sugar beet and then purified and crystallized. Other commercial sources are sorghum, date palm, and sugar maples. The monosaccharides, such as glucose (which is produced from sucrose by enzymes or acid hydrolysis), are a store of energy that is used by biological cells. Oxidation of glucose is known as glycolysis. It occurs in virtually all cells. Glucose is oxidized to either lactate or pyruvate. Under aerobic conditions, the dominant product in most tissues is pyruvate and the pathway is known as aerobic glycolysis. When oxygen is depleted, as for instance during prolonged vigorous exercise, the dominant glycolytic product in many tissues is lactate and the process is known as anaerobic glycolysis. Other sugars besides glucose, such as fructose, can enter glycolysis after being converted to appropriate intermediates that can enter the pathway. Glycolysis results in production of NADH and ATP. The NADH generated during glycolysis is used to fuel mitochondrial ATP synthesis via oxidative phosphorylation. ATP powers virtually every activity of the cell and organism. Organisms from the simplest bacteria to humans use ATP as their primary energy currency.

SUMMARY

This document provides methods and materials related to modulating sugar levels in plants. For example, this document provides plants having increased levels of sugars, plant cells and seeds having the ability to grow into plants having increased levels of sugars, plant products (e.g., sugar extracts, sugar syrup, molasses, food, foodstuffs, and animal feed) having increased levels of sugars, and methods for making such plants, plant cells, and plant products. Plants having the ability to produce increased levels of sugars can be used as sugar sources or sources of plant products having increased levels of sugars. For example, making sugars from plants having the ability to produce increased levels of sugars can allow sugar manufacturers to increase sugar yields (e.g., tons of sugar per acre). In addition, plants and plant products having increased levels of sugars can be used as foods or ingredients in food products having increased nutritional value and flavor per serving.

In one embodiment, a method of modulating the level of a sugar in a plant is provided. The method can include introducing into a plant cell an isolated nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:10, SEQ ID NO:6, SEQ ID NO:11, SEQ ID NO:4, Ceres clone SEQ ID NO:9, SEQ ID NO:7, SEQ ID NO:12, SEQ ID NO:3, SEQ ID NO:8, and the Consensus sequence set forth in FIG. 6, where a plant produced from the plant cell has a different sugar level as compared to a sugar level in a corresponding control plant that does not include the isolated nucleic acid. The sequence identity can be 85 percent or greater, 90 percent or greater, or 95 percent or greater.

In another embodiment, a method of modulating the level of a sugar in a plant is provided. The method can include introducing into a plant cell an isolated nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:10, SEQ ID NO:6, SEQ ID NO:11, SEQ ID NO:4, SEQ ID NO:9, and the Consensus sequence set forth in FIG. 6, where a plant produced from the plant cell has a different sugar level as compared to a sugar level in a corresponding control plant that does not include the isolated nucleic acid. The sequence identity can be 85 percent or greater, 90 percent or greater, or 95 percent or greater.

In another embodiment, a method of modulating the level of a sugar in a plant is provided. The method can include introducing into a plant cell an isolated nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:6, SEQ ID NO:4, and the Consensus sequence set forth in FIG. 6, where a plant produced from the plant cell has a different sugar level as compared to a sugar level in a corresponding control plant that does not include the isolated nucleic acid. The sequence identity can be 85 percent or greater, 90 percent or greater, or 95 percent or greater.

In a further embodiment, a method of modulating the level of a sugar in a plant is provided. The method can include introducing into a plant cell an isolated nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:6, and SEQ ID NO:4, where a plant produced from the plant cell has a different sugar level as compared to a sugar level in a corresponding control plant that does not include the isolated nucleic acid. The sequence identity can be 85 percent or greater, 90 percent or greater, or 95 percent or greater.

In another aspect, a method of modulating the level of a sugar in a plant is provided. The method can include introducing into a plant cell an isolated nucleic acid including a nucleic acid sequence encoding a polypeptide including an amino acid sequence corresponding to SEQ ID NO:2, where a plant produced from the plant cell has a different sugar level as compared to a sugar level in a corresponding control plant that does not include the isolated nucleic acid.

In another aspect, a method of modulating the level of a sugar in a plant is provided. The method can include introducing into a plant cell an isolated nucleic acid including a nucleic acid sequence encoding a polypeptide including an amino acid sequence corresponding to SEQ ID NO:14, where a plant produced from the plant cell has a different sugar level as compared to a sugar level in a corresponding control plant that does not include the isolated nucleic acid.

In yet another aspect, a method of modulating the level of a sugar in a plant is provided. The method can include introducing into a plant cell an isolated nucleic acid including a nucleic acid sequence encoding a polypeptide including an amino acid sequence corresponding to the Consensus sequence set forth in FIG. 6, where a plant produced from the plant cell has a different sugar level as compared to a sugar level in a corresponding control plant that does not include the isolated nucleic acid.

In another embodiment, a method of modulating the level of a sugar in a plant is provided. The method can include introducing into a plant cell (a) a first isolated nucleic acid including a nucleic acid sequence encoding a polypeptide having 80 percent or greater sequence identity to an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, SEQ ID NO:8, and the Consensus sequence set forth in FIG. 6; and (b) a second isolated nucleic acid including a nucleic acid sequence encoding a polypeptide having 80 percent or greater sequence identity to an amino acid sequence corresponding to SEQ ID NO:14; where a plant produced from the plant cell has a different sugar level as compared to a sugar level in a corresponding control plant that does not include the first isolated nucleic acid or the second isolated nucleic acid.

In a further embodiment, a method of modulating the level of a sugar in a plant is provided. The method can include introducing into a plant cell (a) a first isolated nucleic acid including a nucleic acid sequence encoding a polypeptide including an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, SEQ ID NO:8, and the Consensus sequence set forth in FIG. 6; and (b) a second isolated nucleic acid including a nucleic acid sequence encoding a polypeptide including an amino acid sequence corresponding to SEQ ID NO:14; where a plant produced from the plant cell has a different sugar level as compared to a sugar level in a corresponding control plant that does not include the first isolated nucleic acid or the second isolated nucleic acid.

In another embodiment, a method of modulating the level of a sugar in a plant is provided. The method can include introducing into a plant cell (a) a first isolated nucleic acid including a nucleic acid sequence encoding a polypeptide having 80 percent or greater sequence identity to an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, and SEQ ID NO:8; and (b) a second isolated nucleic acid including a nucleic acid sequence encoding a polypeptide having 80 percent or greater sequence identity to an amino acid sequence corresponding to SEQ ID NO:14; where a plant produced from the plant cell has a different sugar level as compared to a sugar level in a corresponding control plant that does not include the first isolated nucleic acid or the second isolated nucleic acid.

In yet another embodiment, a method of modulating the level of a sugar in a plant is provided. The method can include introducing into a plant cell (a) a first isolated nucleic acid including a nucleic acid sequence encoding a polypeptide including an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, and SEQ ID NO:8; and (b) a second isolated nucleic acid including a nucleic acid sequence encoding a polypeptide including an amino acid sequence corresponding to SEQ ID NO:14; where a plant produced from the plant cell has a different sugar level as compared to a sugar level in a corresponding control plant that does not include the first isolated nucleic acid or the second isolated nucleic acid.

A different sugar level can be an increased level of one or more sugars, such as glucose, fructose, or sucrose. A different sugar level can be an increased level of glucose and fructose, or an increased level of glucose, fructose, and sucrose.

In another embodiment, a method of producing a plant having a modulated level of a sugar is provided. The method can include (a) introducing into a plant cell an isolated nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:10, SEQ ID NO:6, SEQ ID NO:11, SEQ ID NO:4, SEQ ID NO:9, SEQ ID NO:7, SEQ ID NO:12, SEQ ID NO:3, SEQ ID NO:8, and the Consensus sequence set forth in FIG. 6; and (b) growing a plant from the plant cell. The sequence identity can be 85 percent or greater, 90 percent or greater, or 95 percent or greater.

In another embodiment, a method of producing a plant having a modulated level of a sugar is provided. The method can include (a) introducing into a plant cell an isolated nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:10, SEQ ID NO:6, SEQ ID NO:11, SEQ ID NO:4, SEQ ID NO:9, and the Consensus sequence set forth in FIG. 6; and (b) growing a plant from the plant cell. The sequence identity can be 85 percent or greater, 90 percent or greater, or 95 percent or greater.

In a further embodiment, a method of producing a plant having a modulated level of a sugar is provided. The method can include (a) introducing into a plant cell an isolated nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:6, SEQ ID NO:4, and the Consensus sequence set forth in FIG. 6; and (b) growing a plant from the plant cell. The sequence identity can be 85 percent or greater, 90 percent or greater, or 95 percent or greater.

In another aspect, a method of producing a plant having a modulated level of a sugar is provided. The method can include (a) introducing into a plant cell an isolated nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:6, and SEQ ID NO:4; and (b) growing a plant from the plant cell. The sequence identity can be 85 percent or greater, 90 percent or greater, or 95 percent or greater.

In another aspect, a method of producing a plant having a modulated level of a sugar is provided. The method can include (a) introducing into a plant cell an isolated nucleic acid including a nucleic acid sequence encoding a polypeptide including an amino acid sequence corresponding to SEQ ID NO:14; and (b) growing a plant from the plant cell.

In another aspect, a method of producing a plant having a modulated level of a sugar is provided. The method can include (a) introducing into a plant cell an isolated nucleic acid including a nucleic acid sequence encoding a polypeptide including an amino acid sequence corresponding to SEQ ID NO:2; and (b) growing a plant from the plant cell.

In yet another aspect, a method of producing a plant having a modulated level of a sugar is provided. The method can include (a) introducing into a plant cell an isolated nucleic acid including a nucleic acid sequence encoding a polypeptide including an amino acid sequence corresponding to the Consensus sequence set forth in FIG. 6; and (b) growing a plant from the plant cell.

In another embodiment, a method of producing a plant having a modulated level of a sugar is provided. The method can include (a) introducing into a plant cell a first isolated nucleic acid including a nucleic acid sequence encoding a polypeptide having 80 percent or greater sequence identity to an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, SEQ ID NO:8, and the Consensus sequence set forth in FIG. 6, and a second isolated nucleic acid including a nucleic acid sequence encoding a polypeptide having 80 percent or greater sequence identity to an amino acid sequence corresponding to SEQ ID NO:14; and (b) growing a plant from the plant cell.

In a further embodiment, a method of producing a plant having a modulated level of a sugar is provided. The method can include (a) introducing into a plant cell a first isolated nucleic acid including a nucleic acid sequence encoding a polypeptide including an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, SEQ ID NO:8, and the Consensus sequence set forth in FIG. 6, and a second isolated nucleic acid including a nucleic acid sequence encoding a polypeptide including an amino acid sequence corresponding to SEQ ID NO:14; and (b) growing a plant from the plant cell.

In another embodiment, a method of producing a plant having a modulated level of a sugar is provided. The method can include (a) introducing into a plant cell a first isolated nucleic acid including a nucleic acid sequence encoding a polypeptide having 80 percent or greater sequence identity to an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, and SEQ ID NO:8, and a second isolated nucleic acid including a nucleic acid sequence encoding a polypeptide having 80 percent or greater sequence identity to an amino acid sequence corresponding to SEQ ID NO:14; and (b) growing a plant from the plant cell.

In yet another embodiment, a method of producing a plant having a modulated level of a sugar is provided. The method can include (a) introducing into a plant cell a first isolated nucleic acid including a nucleic acid sequence encoding a polypeptide including an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, and SEQ ID NO:8, and a second isolated nucleic acid including a nucleic acid sequence encoding a polypeptide including an amino acid sequence corresponding to SEQ ID NO:14; and (b) growing a plant from the plant cell.

A modulated sugar level can be an increased level of one or more sugars, such as glucose, fructose, or sucrose. A modulated sugar level can be an increased level of glucose and fructose, or an increased level of glucose, fructose, and sucrose.

An isolated nucleic acid or an exogenous nucleic acid can be operably linked to a regulatory region, such as a promoter. The promoter can be a broadly expressing promoter, such as p326, YP0158, YP0214, YP0380, PT0848, PT0633, YP0050, YP0144, or YP0190. A promoter can be a cell-specific or tissue-specific promoter, such as a seed-specific promoter, a root-specific promoter, or a non-seed fruit tissue promoter. A seed-specific promoter can be the napin promoter, the Arcelin-5 promoter, the phaseolin gene promoter, the soybean trypsin inhibitor promoter, the ACP promoter, the stearoyl-ACP desaturase gene, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, or the barley hordein gene promoter. A root-specific promoter can be the root specific subdomains of the CaMV 35S promoter or the tobacco RD2 gene promoter. A non-seed fruit tissue promoter can be a polygalacturonidase promoter, the banana TRX promoter, or the melon actin promoter. A promoter can be a constitutive promoter, such as 35S, p32449, or p13879. A promoter can be an inducible promoter.

Plant cells are also provided. In one embodiment, a plant cell can include an exogenous nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:10, SEQ ID NO:6, SEQ ID NO:11, SEQ ID NO:4, SEQ ID NO:9, SEQ ID NO:7, SEQ ID NO:12, SEQ ID NO:3, SEQ ID NO:8, and the Consensus sequence set forth in FIG. 6, where expression of the exogenous nucleic acid in a plant produced from the plant cell is effective to result in a different sugar level as compared to a sugar level in a corresponding control plant that does not include the exogenous nucleic acid. The sequence identity can be 85 percent or greater, 90 percent or greater, or 95 percent or greater.

In another embodiment, a plant cell is provided. The plant cell can include an exogenous nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:10, SEQ ID NO:6, (SEQ ID NO:11, SEQ ID NO:4, SEQ ID NO:9, and the Consensus sequence set forth in FIG. 6, where expression of the exogenous nucleic acid in a plant produced from the plant cell is effective to result in a different sugar level as compared to a sugar level in a corresponding control plant that does not include the exogenous nucleic acid. The sequence identity can be 85 percent or greater, 90 percent or greater, or 95 percent or greater.

In another aspect, a plant cell is provided. The plant cell can include an exogenous nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:6, SEQ ID NO:4, and the Consensus sequence set forth in FIG. 6, where expression of the exogenous nucleic acid in a plant produced from the plant cell is effective to result in a different sugar level as compared to a sugar level in a corresponding control plant that does not include the exogenous nucleic acid. The sequence identity can be 85 percent or greater, 90 percent or greater, or 95 percent or greater.

In yet another embodiment, a plant cell is provided. The plant cell can include an exogenous nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:6, and SEQ ID NO:4, where expression of the exogenous nucleic acid in a plant produced from the plant cell is effective to result in a different sugar level as compared to a sugar level in a corresponding control plant that does not include the exogenous nucleic acid. The sequence identity can be 85 percent or greater, 90 percent or greater, or 95 percent or greater.

In a further embodiment, a plant cell is provided. The plant cell can include an exogenous nucleic acid including a nucleic acid sequence encoding a polypeptide including an amino acid sequence corresponding to SEQ ID NO:2, where expression of the exogenous nucleic acid in a plant produced from the plant cell is effective to result in a different sugar level as compared to a sugar level in a corresponding control plant that does not include the exogenous nucleic acid.

In another embodiment, a plant cell is provided. The plant cell can include an exogenous nucleic acid including a nucleic acid sequence encoding a polypeptide including an amino acid sequence corresponding to SEQ ID NO:14, where expression of the exogenous nucleic acid in a plant produced from the plant cell is effective to result in a different sugar level as compared to a sugar level in a corresponding control plant that does not include the exogenous nucleic acid.

In another aspect, a plant cell is provided. The plant cell can include an exogenous nucleic acid including a nucleic acid sequence encoding a polypeptide including an amino acid sequence corresponding to the Consensus sequence set forth in FIG. 6, where expression of the exogenous nucleic acid in a plant produced from the plant cell is effective to result in a different sugar level as compared to a sugar level in a corresponding control plant that does not include the exogenous nucleic acid.

In still another aspect, a plant cell is provided. The plant cell can include (a) a first exogenous nucleic acid including a nucleic acid sequence encoding a polypeptide having 80 percent or greater sequence identity to an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, SEQ ID NO:8, and the Consensus sequence set forth in FIG. 6; and (b) a second exogenous nucleic acid including a nucleic acid sequence encoding a polypeptide having 80 percent or greater sequence identity to an amino acid sequence corresponding to SEQ ID NO:14; where expression of the first exogenous nucleic acid and the second exogenous nucleic acid in a plant produced from the plant cell is effective to result in a different sugar level as compared to a sugar level in a corresponding control plant that does not include the first exogenous nucleic acid or the second exogenous nucleic acid.

In another embodiment, a plant cell is provided. The plant cell can include (a) a first exogenous nucleic acid including a nucleic acid sequence encoding a polypeptide including an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, SEQ ID NO:8, and the Consensus sequence set forth in FIG. 6; and (b) a second exogenous nucleic acid including a nucleic acid sequence encoding a polypeptide including an amino acid sequence corresponding to SEQ ID NO:14; where expression of the first exogenous nucleic acid and the second exogenous nucleic acid in a plant produced from the plant cell is effective to result in a different sugar level as compared to a sugar level in a corresponding control plant that does not include the first exogenous nucleic acid or the second exogenous nucleic acid.

In another embodiment, a plant cell is provided. The plant cell can include (a) a first exogenous nucleic acid including a nucleic acid sequence encoding a polypeptide having 80 percent or greater sequence identity to an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, and SEQ ID NO:8; and (b) a second exogenous nucleic acid including a nucleic acid sequence encoding a polypeptide having 80 percent or greater sequence identity to an amino acid sequence corresponding to SEQ ID NO:14; where expression of the first exogenous nucleic acid and the second exogenous nucleic acid in a plant produced from the plant cell is effective to result in a different sugar level as compared to a sugar level in a corresponding control plant that does not include the first exogenous nucleic acid or the second exogenous nucleic acid.

In yet another embodiment, a plant cell is provided. The plant cell can include (a) a first exogenous nucleic acid including a nucleic acid sequence encoding a polypeptide including an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, and SEQ ID NO:8; and (b) a second exogenous nucleic acid including a nucleic acid sequence encoding a polypeptide including an amino acid sequence corresponding to SEQ ID NO:14; where expression of the first exogenous nucleic acid and the second exogenous nucleic acid in a plant produced from the plant cell is effective to result in a different sugar level as compared to a sugar level in a corresponding control plant that does not include the first exogenous nucleic acid or the second exogenous nucleic acid.

A different sugar level can be an increased level of one or more sugars, such as glucose, fructose, or sucrose. A different sugar level can be an increased level of glucose and fructose, or an increased level of glucose, fructose, and sucrose. An increased level of one or more sugars can be in the non-seed tissue, seed, root, or fruit of a plant produced from a plant cell.

A plant or plant cell can be a member of one of the following genera: *Abies, Agrostis, Allium, Alseodaphne, Anacardium, Ananus, Andropogon, Arabidopsis, Arachis, Apium, Aragrostis, Ascophyllum, Asparagus, Atropa, Avena, Beilschmiedia, Bixa, Brassica, Calendula, Capsicum, Carthamus, Chondrus, Chicorium, Cinnamomum, Citrus, Citrullus, Cocculus, Cocos, Coffea, Corylus, Cracilaria, Croton, Crypthecodinium, Cucumis, Cucurbita, Cunninghamia, Cuphea, Cynodon, Daucus, Dianthus, Duguetia, Elaeis, Enteromorpha, Euphoria, Festuca, Festulolium, Ficus, Fragaria, Fucus, Glaucium, Glycine, Glycyrrhiza, Gossypium, Haematococcus, Helianthus, Heterocallis, Hevea, Himanthalia, Hordeum, Hyoscyamus, Lactuca, Landolphia, Lemna, Linum, Litsea, Lolium, Lycopersicon, Lupinus, Majorana, Malus, Manihot, Medicago, Mentha, Musa, Nicotiana, Odontella, Olea, Oryza, Palmaria, Panicum, Pannesetum, Parthenium, Persea, Petunia, Phaseolus, Phleum, Phoenix, Picea, Pinus, Pistacia, Pisum, Poa, Populus sect., Porphyra, Prunus, Pyrus, Raphanus, Ricinus, Rosa, Rosmarinus, Rubus, Saccharum, Salix, Schizochytrium, Secale, Senecio, Sinapis, Solanum, Sorghum, Spinacia, Spirulina, Stephania,*

*Triticum, Tagetes, Theobroma, Trifolium, Trigonella, Ulva, Undaria, Vaccinium, Vicia, Vigna, Vitis, Zea.*

A plant or plant cell can be a member of one of the following species: *Ananus comosus, Arabidopsis thaliana, Brassica rapa, Brassica napus, Brassica oleracea, Bixa orellana, Calendula officinalis, Cinnamomum camphora, Coffea arabica, Glycine max, Glycyrrhiza glabra, Gossypium hirsutum, Gossypium herbaceum, Lactuca sativa, Lycopersicon esculentum, Mentha piperita, Mentha spicata, Musa paradisiaca, Oryza sativa, Parthenium argentatum, Rosmarinus officinalis, Solanum tuberosum, Theobroma cacao, Triticum aestivum, Vitis vinifera*, and *Zea mays*.

A plant or plant cell can be one of the following: alfalfa, amaranth, apple, beans (including kidney beans, lima beans, dry beans, green beans), broccoli, cabbage, carrot, castor bean, chick peas, cherry, chicory, chocolate, clover, coffee, cotton, cottonseed, crambe, eucalyptus, flax, grape, grapefruit, lemon, lentils, lettuce, linseed, mango, melon (e.g., watermelon, cantaloupe), mustard, orange, peanut, peach, pear, peas, pepper, plum, poplar, potato, rapeseed (high erucic acid and canola), safflower, sesame, soybean, spinach, strawberry, sugarbeet, sunflower, tea, tomato, banana, barley, date palm, field corn, garlic, millet, oat, oil palm, onion, pineapple, popcorn, rice, rye, sorghum, sudangrass, sugarcane, sweet corn, switchgrass, turf grasses, wheat, fir, pine, spruce, brown seaweeds, green seaweeds, red seaweeds, and microalgae.

Transgenic plants having modulated levels of one or more sugars as compared to corresponding control plants are also provided. In one embodiment, a transgenic plant can include an exogenous nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:10, SEQ ID NO:6, SEQ ID NO:11, SEQ ID NO:4, SEQ ID NO:9, SEQ ID NO:7, SEQ ID NO:12, SEQ ID NO:3, SEQ ID NO:8, and the Consensus sequence set forth in FIG. 6. The sequence identity can be 85 percent or greater, 90 percent or greater, or 95 percent or greater.

In another embodiment, a transgenic plant having a modulated level of one or more sugars as compared to a corresponding control plant is provided. The transgenic plant can include an exogenous nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:10, SEQ ID NO:6, SEQ ID NO:11, SEQ ID NO:4, SEQ ID NO:9, and the Consensus sequence set forth in FIG. 6. The sequence identity can be 85 percent or greater, 90 percent or greater, or 95 percent or greater.

In another aspect, a transgenic plant having a modulated level of one or more sugars as compared to a corresponding control plant is provided. The transgenic plant can include an exogenous nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:6, SEQ ID NO:4, and the Consensus sequence set forth in FIG. 6. The sequence identity can be 85 percent or greater, 90 percent or greater, or 95 percent or greater.

In yet another aspect, a transgenic plant having a modulated level of one or more sugars as compared to a corresponding control plant is provided. The transgenic plant can include an exogenous nucleic acid including a nucleic acid sequence encoding a polypeptide having 80 percent or greater sequence identity to an amino acid sequence selected from the group consisting of SEQ ID NO:14, SEQ ID NO:2, SEQ ID NO:5, SEQ ID NO:6, and SEQ ID NO:4. The sequence identity can be 85 percent or greater, 90 percent or greater, or 95 percent or greater.

In another embodiment, a transgenic plant having a modulated level of one or more sugars as compared to a corresponding control plant is provided. The transgenic plant can include an exogenous nucleic acid including a nucleic acid sequence encoding a polypeptide including an amino acid sequence corresponding to SEQ ID NO:2.

In a further embodiment, a transgenic plant having a modulated level of one or more sugars as compared to a corresponding control plant is provided. The transgenic plant can include an exogenous nucleic acid including a nucleic acid sequence encoding a polypeptide including an amino acid sequence corresponding to SEQ ID NO:14.

In another embodiment, a transgenic plant having a modulated level of one or more sugars as compared to a corresponding control plant is provided. The transgenic plant can include an exogenous nucleic acid including a nucleic acid sequence encoding a polypeptide including an amino acid sequence corresponding to the Consensus sequence set forth in FIG. 6.

In yet another embodiment, a transgenic plant having a modulated level of one or more sugars as compared to a corresponding control plant is provided. The transgenic plant can include (a) a first exogenous nucleic acid including a nucleic acid sequence encoding a polypeptide having 80 percent or greater sequence identity to an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, SEQ ID NO:8, and the Consensus sequence set forth in FIG. 6; and (b) a second exogenous nucleic acid including a nucleic acid sequence encoding a polypeptide having 80 percent or greater sequence identity to an amino acid sequence corresponding to SEQ ID NO:14.

In another aspect, a transgenic plant having a modulated level of one or more sugars as compared to a corresponding control plant is provided. The transgenic plant can include (a) a first exogenous nucleic acid including a nucleic acid sequence encoding a polypeptide including an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, SEQ ID NO:8, and the Consensus sequence set forth in FIG. 6; and (b) a second exogenous nucleic acid including a nucleic acid sequence encoding a polypeptide including an amino acid sequence corresponding to SEQ ID NO:14.

In still a further aspect, a transgenic plant having a modulated level of one or more sugars as compared to a corresponding control plant is provided. The transgenic plant can include (a) a first exogenous nucleic acid including a nucleic acid sequence encoding a polypeptide having 80 percent or greater sequence identity to an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, and SEQ ID NO:8; and (b) a second exogenous nucleic acid including a nucleic acid sequence encoding a polypeptide having 80 percent or greater sequence identity to an amino acid sequence corresponding to SEQ ID NO:14.

In yet another aspect, a transgenic plant having a modulated level of one or more sugars as compared to a corresponding control plant is provided. The transgenic plant can include (a) a first exogenous nucleic acid including a nucleic acid sequence encoding a polypeptide including an amino acid sequence selected from the group consisting of SEQ ID NO:5, SEQ ID NO:10, SEQ ID NO:6, SEQ ID NO:11, SEQ ID NO:4, SEQ ID NO:9, SEQ ID NO:2, SEQ ID NO:7, SEQ ID NO:12, SEQ ID NO:3, and SEQ ID NO:8; and (b) a second exogenous nucleic acid including a nucleic acid sequence encoding a polypeptide including an amino acid sequence corresponding to SEQ ID NO:14.

Also provided are transgenic plant products, methods of producing products from transgenic plants, and articles of manufacture produced from transgenic plants. In one embodiment, tissues from a transgenic plant are provided, such as non-seed tissue, stalk, seed, or fruit. In another embodiment, a food product including non-seed tissue from a transgenic plant is provided. In a further embodiment, a food product including seed from a transgenic plant is provided. In another embodiment, animal feed including non-seed tissue or seeds is provided. In yet another embodiment, animal feed derived from a stalk is provided.

In one embodiment, a method of producing a sugar is provided. The method includes extracting a sugar from a transgenic plant provided herein, such as sugarcane or sugarbeet. The extract can be a liquid or a solid. The sugar can be one or more of sucrose, glucose, and/or fructose.

In another embodiment, a method of producing ethanol is provided. The method includes fermenting plant material from a transgenic plant provided herein, such as corn.

In another aspect, articles of manufacture based on transgenic plants are provided, including sugar, molasses, a bag of seeds, a bag of sugar, a bottle of sugar syrup, a liquid extract, or a solid extract.

An isolated nucleic acid is also provided. The isolated nucleic acid can include a nucleic acid sequence encoding a polypeptide having 80 percent or greater sequence identity to an amino acid sequence selected from the group consisting SEQ ID NO:14, SEQ ID NO:2, SEQ ID NO:5, SEQ ID NO:10, SEQ ID NO:6, SEQ ID NO:11, SEQ ID NO:4, SEQ ID NO:9, SEQ ID NO:7, SEQ ID NO:12, SEQ ID NO:3, SEQ ID NO:8, and the Consensus sequence set forth in FIG. 6. A recombinant vector including the nucleic acid is also provided.

Sugar-modulating polypeptides are provided herein. A sugar-modulating polypeptide can include the amino acid sequence corresponding to SEQ ID NO:5. A sugar-modulating polypeptide can include the amino acid sequence corresponding to SEQ ID NO:10. A sugar-modulating polypeptide can include the amino acid sequence corresponding to SEQ ID NO:6. A sugar-modulating polypeptide can include the amino acid sequence corresponding to SEQ ID NO:1. A sugar-modulating polypeptide can include the amino acid sequence corresponding to SEQ ID NO:4. A sugar-modulating polypeptide can include the amino acid sequence corresponding to SEQ ID NO:9. A sugar-modulating polypeptide can include the amino acid sequence corresponding to SEQ ID NO:7. A sugar-modulating polypeptide can include the amino acid sequence corresponding to SEQ ID NO:12. A sugar-modulating polypeptide can include the amino acid sequence corresponding to SEQ ID NO:3. A sugar-modulating polypeptide can include the amino acid sequence corresponding to SEQ ID NO:8. A sugar-modulating polypeptide can include the amino acid sequence corresponding to the Consensus sequence set forth in FIG. 6.

A sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:5. A sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:10. A sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:6. A sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:11. In some cases, a sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:4. A sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:9. In some cases, a sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:7. A sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:12. A sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:3. A sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:8. A sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to the Consensus sequence set forth in FIG. 6.

Nucleic acids encoding sugar-modulating polypeptides are provided herein. Such nucleic acids can be used to transform plant cells. A nucleic acid encoding a polypeptide that includes an amino acid sequence corresponding to SEQ ID NO:5 can be used to transform a plant cell. A nucleic acid encoding a polypeptide that includes an amino acid sequence corresponding to SEQ ID NO:10 can be used to transform a plant cell. A nucleic acid encoding a polypeptide that includes an amino acid sequence corresponding to SEQ ID NO:6 can be used to transform a plant cell. A nucleic acid encoding a polypeptide that includes an amino acid sequence corresponding to SEQ ID NO:11 can be used to transform a plant cell. A nucleic acid encoding a polypeptide that includes an amino acid sequence corresponding to SEQ ID NO:4 can be used to transform a plant cell. A nucleic acid encoding a polypeptide that includes an amino acid sequence corresponding to SEQ ID NO:9 can be used to transform a plant cell. A nucleic acid encoding a polypeptide that includes an amino acid sequence corresponding to SEQ ID NO:7 can be used to transform a plant cell. A nucleic acid encoding a polypeptide that includes an amino acid sequence corresponding to SEQ ID NO:12 can be used to transform a plant cell. A nucleic acid encoding a polypeptide that includes an amino acid sequence corresponding to SEQ ID NO:3 can be used to transform a plant cell. A nucleic acid encoding a polypeptide that includes an amino acid sequence corresponding to SEQ ID NO:8 can be used to transform a plant cell. A nucleic acid encoding a polypeptide that includes an amino acid sequence corresponding to the Consensus sequence set forth in FIG. 6 can be used to transform a plant cell.

A nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:5 can be used to transform a plant cell. In some cases, a nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:10 can be used to transform a plant cell. A nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:6 can be used to transform a plant cell. A nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:11 can be used to transform a plant cell. A nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:4 can be used to transform a plant cell. In some cases, a nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:9 can be used to transform a plant cell. A nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:7 can be used to transform a plant cell. A nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:12 can be used to transform a plant cell. A nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:3 can be used to transform a plant cell. A nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:8 can be used to transform a plant cell. In some cases, a nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to the Consensus sequence set forth in FIG. 6 can be used to transform a plant cell.

A first nucleic acid encoding a polypeptide that includes an amino acid sequence corresponding to SEQ ID NO:5, and a second nucleic acid encoding a polypeptide that includes an amino acid sequence corresponding to SEQ ID NO:14 can be used to transform a plant cell. A first nucleic acid encoding a polypeptide that includes an amino acid sequence corresponding to SEQ ID NO:10, and a second nucleic acid encoding a polypeptide that includes an amino acid sequence corresponding to SEQ ID NO:14 can be used to transform a plant cell. In some cases, a first nucleic acid encoding a polypeptide that includes an amino acid sequence corresponding to SEQ ID NO:6, and a second nucleic acid encoding a polypeptide that includes an amino acid sequence corresponding to SEQ ID NO:14 can be used to transform a plant cell. A first nucleic acid encoding a polypeptide that includes an amino acid sequence corresponding to SEQ ID NO:11, and a second nucleic acid encoding a polypeptide that includes an amino acid sequence corresponding to SEQ ID NO:14 can be used to transform a plant cell. A first nucleic acid encoding a polypeptide that includes an amino acid sequence corresponding to SEQ ID NO:4, and a second nucleic acid encoding a polypeptide that includes an amino acid sequence corresponding to SEQ ID NO:14 can be used to transform a plant cell. A first nucleic acid encoding a polypeptide that includes an amino acid sequence corresponding to SEQ ID NO:9, and a second nucleic acid encoding a polypeptide that includes an amino acid sequence corresponding to SEQ ID NO:14 can be used to transform a plant cell. In some cases, a first nucleic acid encoding a polypeptide that includes an amino acid sequence corresponding to SEQ ID NO:7, and a second nucleic acid encoding a polypeptide that includes an amino acid sequence corresponding to SEQ ID NO:14 can be used to transform a plant cell. A first nucleic acid encoding a polypeptide that includes an amino acid sequence corresponding to SEQ ID NO:12, and a second nucleic acid encoding a polypeptide that includes an amino acid sequence corresponding to SEQ ID NO:14 can be used to transform a plant cell. A first nucleic acid encoding a polypeptide that includes an amino acid sequence corresponding to SEQ ID NO:3, and a second nucleic acid encoding a polypeptide that includes an amino acid sequence corresponding to SEQ ID NO:14 can be used to transform a plant cell. In some cases, a first nucleic acid encoding a polypeptide that includes an amino acid sequence corresponding to SEQ ID NO:8, and a second nucleic acid encoding a polypeptide that includes an amino acid sequence corresponding to SEQ ID NO:14 can be used to transform a plant cell. A first nucleic acid encoding a polypeptide that includes an amino acid sequence corresponding to the Consensus sequence set forth in FIG. 6, and a second nucleic acid encoding a polypeptide that includes an amino acid sequence corresponding to SEQ ID NO:14 can be used to transform a plant cell.

A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:5, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:10, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:6, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:11, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:4, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:9, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:7, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:12, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:3, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:8, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. A first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to the Consensus sequence set forth in FIG. 6, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is the nucleotide sequence of Ceres clone 625627 (SEQ ID NO:13).

FIG. 2 is the amino acid sequence encoded by Ceres clone 625627 (SEQ ID NO:14).

FIG. 3 is the nucleotide sequence of Ceres clone 32380 (SEQ ID NO:1).

FIG. 4 is the amino acid sequence encoded by Ceres clone 32380 (SEQ ID NO:2).

FIGS. 6A-6D depict an alignment of the amino acid sequence of SEQ ID NO:2 with functionally homologous and orthologous amino acid sequences SEQ ID NO:5, SEQ ID NO:10, SEQ ID NO:6, SEQ ID NO:11, SEQ ID NO:7, SEQ ID NO:12, SEQ ID NO:4, SEQ ID NO:9, SEQ ID NO:3, and SEQ ID NO:8. A consensus sequence (SEQ ID NOs:15-20) determined by the alignment is set forth.

DETAILED DESCRIPTION

Figure 5A:
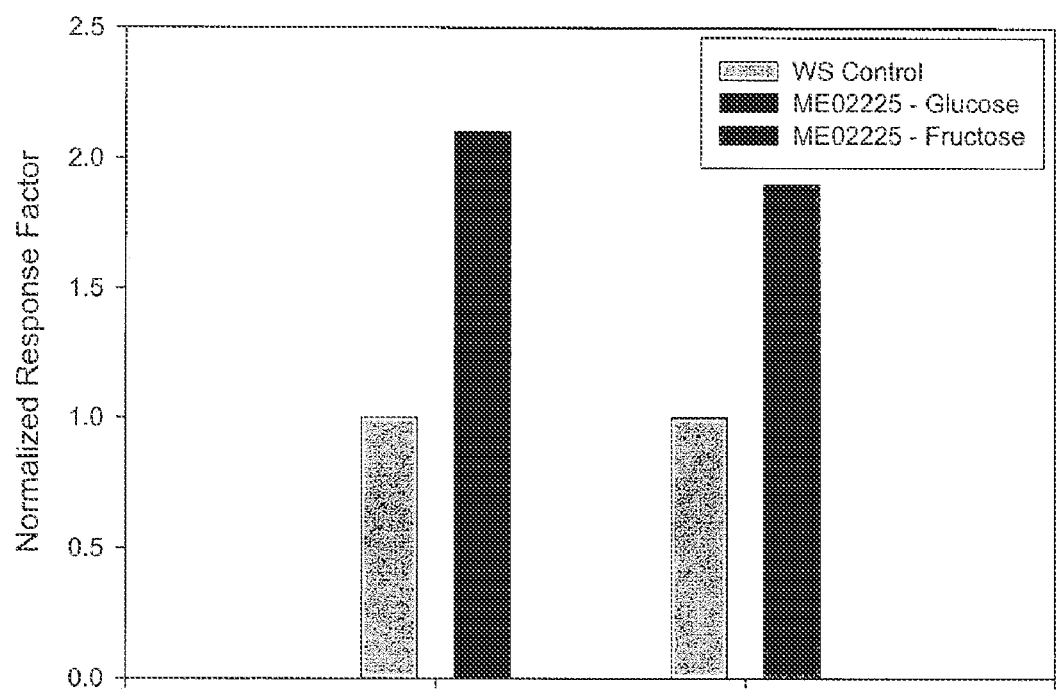
FIG. 5A is a graph plotting levels of glucose and fructose in $T_2$ ME02225 plants relative to control plants.

The materials and methods provided herein can be used to make plants, plant tissues, and plant products having modulated levels of sugars (e.g., glucose, fructose, and sucrose). For example, plants having increased levels of sugars in seeds and/or non-seed tissues are provided herein. The methods can include transforming a plant cell with one or more nucleic acids that encode sugar-modulating polypeptides, wherein expression of the one or more polypeptides results in modulated levels (e.g., increased or decreased levels) of one or more sugars. Plants and plant materials (e.g., seeds, non-seed tissues) produced using such methods can be used as food sources of sugars, or as sources of sugars for inclusion in nutritional supplements, for example.

Polypeptides

Isolated polypeptides, including sugar-modulating polypeptides, are provided herein. The term "polypeptide" as used herein refers to a compound of two or more subunit amino acids, amino acid analogs, or other peptidomimetics, regardless of post-translational modification (e.g., phosphorylation or glycosylation). The subunits may be linked by peptide bonds or other bonds such as, for example, ester or ether bonds. The term "amino acid" refers to natural and/or unnatural or synthetic amino acids, including D/L optical isomers. Full-length proteins, analogs, mutants, and fragments thereof are encompassed by this definition.

By "isolated" or "purified" with respect to a polypeptide it is meant that the polypeptide is separated to some extent from the cellular components with which it is normally found in nature (e.g., other polypeptides, lipids, carbohydrates, and nucleic acids). A purified polypeptide can yield a single major band on a non-reducing polyacrylamide gel. A purified polypeptide can be at least about 75 percent pure (e.g., at least 80 percent, 85 percent, 90 percent, 95 percent, 97 percent, 98 percent, 99 percent, or 100 percent pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

Described herein are sugar-modulating polypeptides. A sugar-modulating polypeptide can be effective to modulate a level of one or more sugars by any mechanism. For example, a sugar-modulating polypeptide can modulate sugar biosynthesis, stability, and/or degradation. In some cases, such a polypeptide is a transcription factor containing an AP2 DNA-binding domain. An AP2 DNA-binding domain is a distinguishing characteristic of a family of transcription factors unique to plants. The prototypic members of the family are AP2 (APETALA2) and EREBPs (ethylene-responsive element binding proteins). AP2/REBP genes form a large multigene family, and they play a variety of roles throughout the plant life cycle: from being key regulators of several developmental processes, like floral organ identity determination or control of leaf epidermal cell identity, to forming part of the mechanisms used by plants to respond to various types of biotic and environmental stress.

SEQ ID NO:14 shown in FIG. 2 sets forth the amino acid sequence of a clone identified herein as Ceres clone 625627, which is predicted to include an AP2 DNA-binding domain. A sugar-modulating polypeptide can be a polypeptide including the amino acid sequence set forth in SEQ ID NO:14. Alternatively, a sugar-modulating polypeptide can be an ortholog, homolog, or variant of the polypeptide having the sequence set forth in SEQ ID NO:14. For example, a sugar-modulating polypeptide can have an amino acid sequence with at least 60 percent sequence identity (e.g., 61 percent, 66 percent, 68 percent, 70 percent, 72 percent, 74 percent, 76 percent, 78 percent, 80 percent, 81 percent, 82 percent, 83 percent, 84 percent, 85 percent, 86 percent, 87 percent, 88 percent, 89 percent, 90 percent, 91 percent, 92 percent, 93 percent, 94 percent, 95 percent, 96 percent, 97 percent, 98 percent, or 99 percent sequence identity) to the amino acid sequence set forth in SEQ ID NO:14.

In other cases, a sugar-modulating polypeptide is a DNA-directed RNA polymerase, such as DNA-directed RNA polymerase II. A DNA-directed RNA polymerase catalyzes the transcription of DNA into RNA.

SEQ ID NO:2 shown in FIG. 4 sets forth the amino acid sequence of an *Arabidopsis* clone identified herein as Ceres clone 32380, which is predicted to include a DNA-directed RNA polymerase II third largest subunit. Homologs and orthologs of the polypeptide having the amino acid sequence set forth in SEQ ID NO:2 are provided in FIG. 6.

A sugar-modulating polypeptide can be a polypeptide including the amino acid sequence set forth in SEQ ID NO:2. Alternatively, a sugar-modulating polypeptide can be an ortholog, homolog, or variant of the polypeptide having the sequence set forth in SEQ ID NO:2. For example, a sugar-modulating polypeptide can have an amino acid sequence with at least 60 percent sequence identity (e.g., 61 percent, 66 percent, 68 percent, 70 percent, 72 percent, 74 percent, 76 percent, 78 percent, 80 percent, 81 percent, 82 percent, 83 percent, 84 percent, 85 percent, 86 percent, 87 percent, 88 percent, 89 percent, 90 percent, 91 percent, 92 percent, 93 percent, 94 percent, 95 percent, 96 percent, 97 percent, 98 percent, or 99 percent sequence identity) to the amino acid sequence set forth in SEQ ID NO:2. For example, a sugar-modulating polypeptide can include the amino acid sequence corresponding to Ceres clone 698259 (SEQ ID NO:5), Ceres clone 698259T (SEQ ID NO:10), Ceres clone 244359 (SEQ ID NO:6), Ceres clone 244359T (SEQ ID NO:11), Ceres clone 692249 (SEQ ID NO:4), Ceres clone 692249T (SEQ ID NO:9), gi|50898416 (SEQ ID NO:7), gi|50898416T (SEQ ID NO:12), gi|21593370 (SEQ ID NO:3), gi|21593370T (SEQ ID NO:8), or the Consensus sequence set forth in FIG. 6.

In some cases, a sugar-modulating polypeptide can include a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:5, SEQ ID NO:10, SEQ ID NO:6, SEQ ID NO:1, SEQ ID NO:4, SEQ ID NO:9, SEQ ID NO:7, SEQ ID NO:12, SEQ ID NO:3, SEQ ID NO:8, or the Consensus sequence set forth in FIG. 6.

A consensus amino acid sequence for a sugar-modulating polypeptide can be determined by aligning homologous and/or orthologous amino acid sequences (e.g., amino acid sequences set forth in FIG. 6) and determining the most common amino acid or type of amino acid at each position. For example, a consensus sequence can be determined by aligning amino acid sequences corresponding to SEQ ID NO:5, SEQ ID NO:10, SEQ ID NO:6, SEQ ID NO:1, SEQ ID NO:7, SEQ ID NO:12, SEQ ID NO:4, SEQ ID NO:9, SEQ ID NO:2, SEQ ID NO:3, and SEQ ID NO:8 as shown in FIG. 6.

Other means by which sugar-modulating polypeptides can be identified include functional complementation of sugar-modulating polypeptide mutants. Suitable sugar-modulating polypeptides also can be identified by analysis of nucleotide and polypeptide sequence alignments. For example, performing a query on a database of nucleotide or polypeptide sequences can identify homologs and/or orthologs of the polypeptide having the amino acid sequence set forth in SEQ ID NO:2. Sequence analysis can involve BLAST, Reciprocal BLAST, or PSI-BLAST analysis of nonredundant databases. Those proteins in the database that have greater than 35% sequence identity to the specific query polypeptide can be candidates for further evaluation for suitability as sugar-modulating polypeptides. If desired, manual inspection of such candidates can be carried out in order to reduce the number of candidates to be further evaluated. Manual inspection can be performed by selecting those candidates that appear to have domains suspected of being present in sugar-modulating polypeptides.

Typically, conserved regions of sugar-modulating polypeptides exhibit at least 40 percent amino acid sequence identity (e.g., at least 45 percent, at least 50 percent, at least 60 percent, at least 70 percent, at least 80 percent, or at least 90 percent amino acid sequence identity). Conserved regions of target and template polypeptides can exhibit at least 92 percent, 94 percent, 96 percent, 98 percent, or 99 percent amino acid sequence identity. Amino acid sequence identity can be deduced from amino acid or nucleotide sequences. In certain cases, highly conserved domains can be identified within sugar-modulating polypeptides. These conserved regions can be useful in identifying functionally similar polypeptides.

Domains are groups of contiguous amino acids in a polypeptide that can be used to characterize protein families and/or parts of proteins. Such domains have a "fingerprint" or "signature" that can comprise conserved (1) primary sequence, (2) secondary structure, and/or (3) three-dimensional conformation. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed.

The identification of conserved regions in a template, or subject, polypeptide can facilitate production of variants of wild type sugar-modulating polypeptides. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Pfam/ and online at genome.wustl.edu/Pfam/. Descriptions of the information included at the Pfam database are included in Sonnhammer et al., 1998, Nucl. Acids Res. 26:320-322; Sonnhammer et al., 1997, Proteins 28:405-420; and Bateman et al., 1999, Nucl. Acids Res. 27:260-262. From the Pfam database, consensus sequences of protein motifs and domains can be aligned with the template polypeptide sequence to determine conserved region(s).

Conserved regions also can be determined by aligning sequences of the same or related polypeptides from closely related species. Closely related species preferably are from the same family. In some embodiments, alignment of sequences from two different species is adequate. For example, sequences from *Arabidopsis* and *Zea mays* can be used to identify one or more conserved regions.

If desired, the classification of a polypeptide as a sugar-modulating polypeptide can be determined using techniques known to those having ordinary skill in the art. These techniques can be divided into two general categories: global sugar analysis, and type-specific sugar analysis. Global sugar analysis techniques can include determining the overall level of sugars within a cell, group of cells, or tissue (e.g., non-seed tissue vs. seed tissue). Type-specific sugar analysis techniques can include measuring the level of a particular type of sugar (i.e., glucose, fructose, or sucrose).

Polynucleotides

Isolated nucleic acids are also provided herein, including isolated nucleic acids that encode any of the sugar-modulating polypeptides described herein. The terms "nucleic acid" and "polynucleotide" are used interchangeably herein, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

As used herein, "isolated," when in reference to a nucleic acid, refers to a nucleic acid that is separated from other nucleic acids that are present in a genome, e.g., a plant genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by the polymerase chain reaction (PCR) or restriction endonuclease treatment) independent of other sequences, as well as DNA that is incorporated into a vector, an autonomously replicating plasmid, a virus (e.g., pararetrovirus, retrovirus, lentivirus, adenovirus, adeno-associated virus, or herpesvirus), or the purified genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid can be made, for example, by chemical synthesis or using PCR. PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

The term "exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory regions flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Thus, provided herein are nucleic acids encoding any of the sugar-modulating polypeptides described previously One example of an isolated polynucleotide is SEQ ID NO:13 shown in FIG. 1, which sets forth the nucleotide sequence of a clone identified herein as Ceres clone 625627. Another example of an isolated polynucleotide is SEQ ID NO:1 shown in FIG. 3, which sets forth the nucleotide sequence of an *Arabidopsis*clone identified herein as Ceres clone 32380. Fragments, fusions, complements, and reverse complements of the described polynucleotides (and encoded polypeptides) also are contemplated.

One or more nucleic acids that encode sugar-modulating polypeptides can be used to transform a plant cell such that a plant produced from the plant cell has a modulated (e.g., increased) level of one or more sugars. For example, a nucleic acid encoding a polypeptide that includes an amino acid sequence corresponding to SEQ ID NO:14 can be used to transform a plant cell. A nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can also be used to transform a plant cell.

In certain cases, a nucleic acid encoding a polypeptide that includes an amino acid sequence corresponding to SEQ ID NO:2 can be used to transform a plant cell. In other cases, a nucleic acid encoding a polypeptide that includes an amino acid sequence corresponding to SEQ ID NO:5, SEQ ID NO:10, SEQ ID NO:6, SEQ ID NO:11, SEQ ID NO:4, SEQ ID NO:9, SEQ ID NO:7, SEQ ID NO:12, SEQ ID NO:3, SEQ ID NO:8, or the Consensus sequence set forth in FIG. 6 can be used to transform a plant cell.

In some cases, a nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:2 can be used to transform a plant cell. In yet other cases, a nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:5, SEQ ID NO:10, SEQ ID NO:6, SEQ ID NO:1, SEQ ID NO:4, SEQ ID NO:9, SEQ ID NO:7, SEQ ID NO:12, SEQ ID NO:3, SEQ ID NO:8, or the Consensus sequence set forth in FIG. 6 can be used to transform a plant cell.

Two or more nucleic acids that encode sugar-modulating polypeptides can also be used to transform a plant cell such that a plant produced from the plant cell has a modulated (e.g., increased) level of one or more sugars. For example, a first nucleic acid encoding a polypeptide that includes an amino acid sequence corresponding to SEQ ID NO:2, and a second nucleic acid encoding a polypeptide that includes an amino acid sequence corresponding to SEQ ID NO:14 can be used to transform a plant cell. In certain embodiments, a first nucleic acid encoding a polypeptide that includes an amino acid sequence corresponding to SEQ ID NO:5, SEQ ID NO:10, SEQ ID NO:6, SEQ ID NO:11, SEQ ID NO:4, SEQ ID NO:9, SEQ ID NO:7, SEQ ID NO:12, SEQ ID NO:3, SEQ ID NO:8, or the Consensus sequence set forth in FIG. 6, and a second nucleic acid encoding a polypeptide that includes an amino acid sequence corresponding to SEQ ID NO:14 can be used to transform a plant cell.

In yet other cases, a first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:2, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell. In addition, a first nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:5, SEQ ID NO:10, SEQ ID NO:6, SEQ ID NO:11, SEQ ID NO:4, SEQ ID NO:9, SEQ ID NO:7, SEQ ID NO:12, SEQ ID NO:3, SEQ ID NO:8, or the Consensus sequence set forth in FIG. 6, and a second nucleic acid encoding a polypeptide having at least 80 percent sequence identity (e.g., 80 percent, 85 percent, 90 percent, 93 percent, 95 percent, 97 percent, 98 percent, or 99 percent sequence identity) to an amino acid sequence corresponding to SEQ ID NO:14 can be used to transform a plant cell.

It will be appreciated that methods described herein can utilize non-transgenic plant cells or plants that carry a mutation in a sugar-modulating polypeptide. For example, a plant carrying a T-DNA insertion, a deletion, a transversion mutation, or a transition mutation in the coding sequence for one of the aforementioned polypeptides can affect sugar levels.

As used herein, the term "percent sequence identity" refers to the degree of identity between any given query sequence and a subject sequence. A percent identity for any query nucleic acid or amino acid sequence, e.g., a sugar-modulating polypeptide, relative to another subject nucleic acid or amino acid sequence can be determined as follows. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; and gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw). To determine a "percent identity" between a query sequence and a subject sequence, the number of matching bases or amino acids in the alignment is divided by the total number of matched and mismatched bases or amino acids, followed by multiplying the result by 100.

It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Recombinant Constructs, Vectors and Host Cells

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper regulatory regions. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes one or more regulatory regions. Suitable expression vectors include, without limitation, plasmids and viral vectors derived from, for example, bacteriophage, baculoviruses, tobacco mosaic virus, herpesviruses, cytomegalovirus, vaccinia viruses, adenoviruses, adeno-associated viruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The term "regulatory region" refers to nucleotide sequences that influence transcription or translation initiation and rate, and stability and/or mobility of the transcript or polypeptide product. Regulatory regions include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, introns, and other regulatory regions that can reside within coding sequences, such as secretory signals and protease cleavage sites.

As used herein, the term "operably linked" refers to positioning of a regulatory region and a transcribable sequence in a nucleic acid so as to allow or facilitate transcription of the transcribable sequence. For example, a regulatory region is operably linked to a coding sequence when RNA polymerase is able to transcribe the coding sequence into mRNA, which then can be translated into a protein encoded by the coding sequence.

Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter. A promoter can, however, be positioned as much as about 5,000 nucleotides upstream of the translation start site, or about 2,000 nucleotides upstream of the transcription start site. A promoter typically comprises at least a core (basal) promoter. A promoter also may include at least one control element such as an upstream element. Such elements include upstream activation regions (UARs) and, optionally, other DNA sequences that affect transcription of a polynucleotide such as a synthetic upstream element. The choice of promoters to be included depends upon several factors, including, but not limited to, efficiency, selectability, inducibility, desired expression level, and cell or tissue specificity.

Constitutive Promoters

Constitutive promoters can promote transcription of an operably linked nucleic acid under most, but not necessarily all, environmental conditions and states of development or cell differentiation. Non-limiting examples of constitutive promoters that can be included in the nucleic acid constructs provided herein include the cauliflower mosaic virus (CaMV) 35S transcription initiation region, the mannopine synthase (MAS) promoter, the 1' or 2' promoters derived from T-DNA of *Agrobacterium tumefaciens*, the figwort mosaic virus 35S promoter, actin promoters such as the rice actin promoter, ubiquitin promoters such as the maize ubiquitin-1 promoter, p32449, and p13879.

Broadly Expressing Promoters

A promoter can be said to be "broadly expressing" when it promotes transcription in many, but not all, plant tissues. For example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. In certain cases, a broadly expressing promoter operably linked to a sequence can promote transcription of the linked sequence in a plant shoot at a level that is at least two times, e.g., at least 3, 5, 10, or 20 times, greater than the level of transcription in a developing seed. In other cases, a broadly expressing promoter can promote transcription in a plant shoot at a level that is at least two times, e.g., at least 3, 5, 10, or 20 times, greater than the level of transcription in a reproductive tissue of a flower. In view of the above, the CaMV 35S promoter is not considered a broadly expressing promoter. Non-limiting examples of broadly expressing promoters that can be included in the nucleic acid constructs provided herein include the p326, YP0158, YP0214, YP0380, PT0848, PT0633, YP0050, YP0144 and YP0190 promoters. See, e.g., U.S. patent application Ser. No. 11/208,308, filed Aug. 19, 2005.

Tissue-, organ- and cell-specific promoters confer transcription only or predominantly in a particular tissue, organ, and cell type, respectively. In some embodiments, promoters specific to non-seed tissues, such as vegetative tissues, can be suitable regulatory regions. Vegetative tissues include the stem, parenchyma, ground meristem, vascular bundle, cambium, phloem, cortex, shoot apical meristem, lateral shoot meristem, root apical meristem, lateral root meristem, leaf primordium, leaf mesophyll, or leaf epidermis.

Root-Specific Promoters

Root-specific promoters confer transcription only or predominantly in root tissue. Examples of root-specific promoters include the root specific subdomains of the CaMV 35S promoter (Lam et al., Proc Natl Acad Sci USA 86:7890-7894 (1989)), root cell specific promoters reported by Conkling et al. Plant Physiol. 93:1203-1211 (1990), and the tobacco RD2 gene promoter.

Seed-Specific Promoters

In some embodiments, promoters that are essentially specific to seeds can be useful. Transcription from a seed-specific promoter occurs primarily in endosperm and cotyledon tissue during seed development. Non-limiting examples of seed-specific promoters that can be included in the nucleic acid constructs provided herein include the napin promoter, the Arcelin-5 promoter, the phaseolin gene promoter (Bustos et al., Plant Cell 1(9):839-853 (1989)), the soybean trypsin inhibitor promoter (Riggs et al., Plant Cell 1(6):609-621 (1989)), the ACP promoter (Baerson et al., Plant Mol Biol, 22(2):255-267 (1993)), the stearoyl-ACP desaturase gene (Slocombe et al., Plant Physiol 104(4):167-176 (1994)), the soybean α' subunit of β-conglycinin promoter (Chen et al., Proc. Natl. Acad. Sci. U.S.A. 83:8560-8564 (1986)), the oleosin promoter (Hong et al., Plant Mol Biol 34(3):549-555 (1997)), zein promoters such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., Mol. Cell Biol. 13:5829-5842 (1993)), the beta-amylase gene promoter, and the barley hordein gene promoter.

Non-Seed Fruit Tissue Promoters

Promoters that are active in non-seed fruit tissues can also be useful, e.g., a polygalacturonidase promoter, the banana TRX promoter, and the melon actin promoter.

Female Gametophyte Specific Promoters

To achieve female gametophyte specific expression, regulatory elements that preferentially drive transcription in female gametophytic tissues are used, such as embryo sac promoters. Most suitable are regulatory elements that preferentially drive transcription in polar nuclei or the central cell, or in precursors to polar nuclei, but not in egg cells or precursors to egg cells. A regulatory element whose pattern of transcription extends from polar nuclei into early endosperm development is also acceptable, although rapidly diminishing transcription in endosperm tissue after fertilization is most preferred. Expression in the zygote or developing embryo is not preferred.

Female reproductive tissue promoters that may be suitable include those derived from the following genes: maize MAC1 (see, Sheridan (1996) Genetics, 142:1009-1020); maize Cat3 (see, GenBank No. L05934; Abler (1993) Plant Mol. Biol., 22:10131-1038); Arabidopsis viviparous-1 (see, Genbank No. U93215); Arabidopsis atmyc1 (see, Urao (1996) Plant Mol. Biol., 32:571-57; Conceicao (1994) Plant, 5:493-505).

Other female gametophyte tissue promoters include those derived from the following genes: Arabidopsis Fie (GenBank No. AF129516); Arabidopsis Mea; and Arabidopsis Fis2 (GenBank No. AF096096); ovule BEL1 (Reiser (1995) Cell, 83:735-742; Ray (1994) Proc. Natl. Acad. Sci. U.S.A. 91:5761-5765; GenBank No. U39944); Fie 1.1 (U.S. Pat. No. 6,906,244) and Arabidopsis DMC1 (see, GenBank No. U76670). Ovary-specific promoters include the tomato pz7 gene promoter and the tomato pz130 gene promoter. Other exemplary female gametophyte tissue-specific promoters include the following Arabidopsis promoters: YP0039, YP0101, YP0102, YP0110, YP0117, YP0119, YP0137, DME PROMOTER, YP0285 and YP0212. Female gametophyte tissue promoters that may be useful in monocotyledonous plants such as rice include the following promoters: Y678g10, p756a09, Y790g04, p780a10, Y730e07, Y760g09, p530c10, p524d05, p523d11 and p472e10.

Photosynthetically-Active Tissue Promoters

Photosynthetically-active tissue promoters confer transcription only or predominantly in photosynthetically active tissue. Examples of such promoters include the ribulose-1,5-bisphosphate carboxylase (RbcS) promoters such as the RbcS promoter from eastern larch (Larix laricina), the pine cab6 promoter (Yamamoto et al, Plant Cell Physiol. 35:773-778 (1994)), the Cab-1 gene promoter from wheat (Fejes et al., Plant Mol. Biol. 15:921-932 (1990)), the CAB-1 promoter from spinach (Lubberstedt et al., Plant Physiol. 104:997-1006 (1994)), the cab IR promoter from rice (Luan et al., Plant Cell 4:971-981 (1992)), the pyruvate, orthophosphate dikinase (PPDK) promoter from corn (Matsuoka et al., Proc. Natl. Acad. Sci. U.S.A. 90:9586-9590 (1993)), the tobacco Lhcb1*2 promoter (Cerdan et al, Plant Mol. Biol. 33:245-255 (1997)), the Arabidopsis thaliana SUC2 sucrose-H+ symporter promoter (Truernit et al., Planta. 196:564-570 (1995)), and thylakoid membrane protein promoters from spinach (psaD, psaF, psaE, PC, FNR, atpC, atpD, cab, rbcS).

Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Other Promoters

Other classes of promoters include, but are not limited to, inducible promoters, such as promoters that confer transcription in response to external stimuli such as chemical agents, developmental stimuli, or environmental stimuli.

Other suitable promoters include those set forth in U.S. patent application Ser. Nos. 60/505,689; 60/518,075; 60/544,771; 60/558,869; 60/583,691; 60/619,181; 60/637,140; 10/957,569; 11/058,689; 11/172,703 and PCT/US05/23639, e.g., promoters designated YP0086 (gDNA ID 7418340), YP0188 (gDNA ID 7418570), YP0263 (gDNA ID 7418658), p13879, p32449, PT0758; PT0743; PT0829; YP0096 and YP0119.

Other Regulatory Regions

A 5' untranslated region (UTR) is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA message stability or translation attenuation. Examples of 3' UTRs include, but are not limited to polyadenylation signals and transcription termination sequences.

A polyadenylation region at the 3'-end of a coding region can also be operably linked to a coding sequence. The polyadenylation region can be derived from the natural gene, from various other plant genes, or from transfer-DNA (T-DNA).

A suitable enhancer is a cis-regulatory element (−212 to −154) from the upstream region of the octopine synthase (ocs) gene. Fromm et al, *The Plant Cell* 1:977-984 (1989).

The vectors provided herein also can include, for example, origins of replication, scaffold attachment regions (SARs), and/or markers. A marker gene can confer a selectable phenotype on a plant cell. For example, a marker can confer, biocide resistance, such as resistance to an antibiotic (e.g., kanamycin, G418, bleomycin, or hygromycin), or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

It will be understood that more than one regulatory region may be present in a recombinant polynucleotide, e.g., introns, enhancers, upstream activation regions, and inducible elements. Thus, more than one regulatory region can be operably linked to the sequence encoding a sugar-modulating polypeptide.

The recombinant DNA constructs provided herein typically include a polynucleotide sequence (e.g., a sequence encoding a sugar-modulating polypeptide) inserted into a vector suitable for transformation of plant cells. Recombinant vectors can be made using, for example, standard recombinant DNA techniques (see, e.g., Sambrook et al. (1989) *Molecular Cloning: A Laboratory Manual*, 2nd ed., Cold Spring Harbor Laboratory, Cold Spring Harbor, N.Y.).

Transgenic Plants and Cells

Any of the vectors provided herein can be used to transform plant cells and, if desired, generate transgenic plants. Thus, transgenic plants and plant cells containing the nucleic acids described herein also are provided, as are methods for making such transgenic plants and plant cells. A plant or plant cells can be transformed by having the construct integrated into its genome, i.e., can be stably transformed. Stably transformed cells typically retain the introduced nucleic acid sequence with each cell division. Alternatively, the plant or plant cells also can be transiently transformed such that the construct is not integrated into its genome. Transiently transformed cells typically lose some or all of the introduced nucleic acid construct with each cell division, such that the introduced nucleic acid cannot be detected in daughter cells after sufficient number of cell divisions. Both transiently transformed and stably transformed transgenic plants and plant cells can be useful in the methods described herein.

Typically, transgenic plant cells used in the methods described herein constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. Progeny includes descendants of a particular plant or plant line. Progeny of an instant plant include seeds formed on $F_1$, $F_2$, $F_3$, $F_4$, $F_5$, $F_6$, and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants.

Seeds produced by a transgenic plant can be grown and then selfed (or outcrossed and selfed) to obtain seeds homozygous for the nucleic acid construct.

Alternatively, transgenic plant cells can be grown in suspension culture, or tissue or organ culture, for production of secondary metabolites. For the purposes of the methods provided herein, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

Techniques for transforming a wide variety of higher plant species are known in the art. The polynucleotides and/or recombinant vectors described herein can be introduced into the genome of a plant host using any of a number of known methods, including electroporation, microinjection, and biolistic methods. Alternatively, polynucleotides or vectors can be combined with suitable T-DNA flanking regions and introduced into a conventional *Agrobacterium tumefaciens* host vector. Such Agrobacterium tumefaciens-mediated transformation techniques, including disarming and use of binary vectors, are well known in the art. Other gene transfer and transformation techniques include protoplast transformation through calcium or PEG, electroporation-mediated uptake of naked DNA, electroporation of plant tissues, viral vector-mediated transformation, and microprojectile bombardment (see, e.g., U.S. Pat. Nos. 5,538,880; 5,204,253; 5,591,616; and 6,329,571). If a cell or tissue culture is used as the recipient tissue for transformation, plants can be regenerated from transformed cultures using techniques known to those skilled in the art.

The polynucleotides and vectors described herein can be used to transform a number of monocotyledonous and dicotyledonous plants and plant cell systems, including dicots such as alfalfa, amaranth, apple, beans (including kidney beans, lima beans, dry beans, green beans), broccoli, cabbage, carrot, castor bean, chick peas, cherry, chicory, chocolate, clover, coffee, cotton, cottonseed, crambe, eucalyptus, flax, grape, grapefruit, lemon, lentils, lettuce, linseed, mango, melon (e.g., watermelon, cantaloupe), mustard, orange, peanut, peach, pear, peas, pepper, plum, poplar, potato, rapeseed (high erucic acid and canola), safflower, sesame, soybean, spinach, strawberry, sugarbeet, sunflower, tea, tomato, as well as monocots such as banana, barley, date palm, field corn, garlic, millet, oat, oil palm, onion, pineapple, popcorn, rice, rye, sorghum, sudangrass, sugarcane, sweet corn, switchgrass, turf grasses, and wheat. Gymnosperms such as fir, pine and spruce can also be suitable. Brown seaweeds, green seaweeds, red seaweeds, and microalgae also can be used.

Thus, the methods and compositions described herein can be used with dicotyledonous plants belonging, for example, to the orders *Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Illiciales, Juglandales, Lamiales, Laurales, Lecythidales, Leitneriales, Magniolales, Malvales, Myricales, Myrtales, Nymphaeales, Papeverales, Piperales, Plantaginales, Plumbaginales, Podostemales, Polemoniales, Polygalales,*

*Polygonales, Primulales, Proteales, Rafflesiales, Ranunculales, Rhamnales, Rosales, Rubiales, Salicales, Santales, Sapindales, Sarraceniaceae, Scrophulariales, Trochodendrales, Theales, Umbellales, Urticales,* and *Violales.* The methods and compositions described herein also can be utilized with monocotyledonous plants such as those belonging to the orders *Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, Zingiberales,* and with plants belonging to *Gymnospermae,* e.g., *Pinales, Ginkgoales, Cycadales* and *Gnetales.*

The methods and compositions can be used over a broad range of plant species, including species from the dicot genera *Apium, Alseodaphne, Anacardium, Arabidopsis, Arachis, Atropa, Beilschmiedia, Bixa, Brassica, Capsicum, Calendula, Carthamus, Chicorium, Cinnamomum, Citrus, Citrullus, Cocculus, Cocos, Coffea, Corylus, Croton, Cucumis, Cucurbita, Cuphea, Daucus, Dianthus, Duguetia, Euphoria, Ficus, Fragaria, Glaucium, Glycine, Glycyrrhiza, Gossypium, Helianthus, Hevea, Hyoscyamus, Lactuca, Landolphia, Linum, Litsea, Lycopersicon, Lupinus, Majorana, Malus, Manihot, Medicago, Mentha, Nicotiana, Olea, Parthenium, Persea, Petunia, Phaseolus, Pistacia, Pisum, Populus sect., Prunus, Pyrus, Raphanus, Ricinus, Rosa, Rosmarinus, Rubus, Salix, Senecio, Sinapis, Solanum, Spinacia, Stephania, Tagetes, Theobroma, Trifolium, Trigonella, Vaccinium, Vicia, Vigna, Vitis*; and the monocot genera *Allium, Andropogon, Ananus, Aragrostis, Asparagus, Avena, Cynodon, Elaeis, Festuca, Festulolium, Heterocallis, Hordeum, Lemna, Lolium, Musa, Oryza, Panicum, Pannesetum, Phleum, Poa, Phoenix, Saccharum, Secale, Sorghum, Triticum,* and *Zea*; and the gymnosperm genera *Abies, Cunninghamia, Picea,* and *Pinus.*

The methods and compositions described herein also can be used with brown seaweeds, e.g., *Ascophyllum nodosum, Fucus vesiculosus, Fucus serratus, Himanthalia elongata,* and *Undaria pinnatifida*; red seaweeds, e.g., *Porphyra umbilicalis, Palmaria palmata, Cracilaria verrucosa,* and *Chondrus crispus*; green seaweeds, e.g., *Ulva* spp. and *Enteromorpha* spp.; and microalgae, e.g., *Spirulina* sp. (*S. platensis* and *S. maxima*) and *Odontella aurita.* In addition, the methods and compositions can be used with *Cryptheco-dinium cohnii, Schizochytrium* spp., and *Haematococcus pluvialis.*

In some embodiments, a plant can be from a species selected from *Ananus comosus, Arabidopsis thaliana, Brassica rapa, Brassica napus, Brassica oleracea, Bixa orellana, Calendula officinalis, Cinnamomum camphora, Coffea arabica, Glycine max, Glycyrrhiza glabra, Gossypium hirsutum, Gossypium herbaceum, Lactuca sativa, Lycopersicon esculentum, Mentha piperita, Mentha spicata, Musa paradisiaca, Oryza sativa, Parthenium argentatum, Rosmarinus officinalis, Solanum tuberosum, Theobroma cacao, Triticum aestivum, Vitis vinifera,* and *Zea mays.* For example, in certain embodiments, plants from the following species can be preferred: *Ananus comosus, Brassica rapa, Brassica napus, Brassica oleracea, Coffea arabica, Glycine max, Gossypium hirsutum, Gossypium herbaceum, Lactuca sativa, Lycopersicon esculentum, Mentha piperita, Mentha spicata, Musa paradisiaca, Oryza Sativa, Parthenium argentatum, Solanum tuberosum, Theobroma cacao, Triticum aestivum, Vitis vinifera,* and *Zea mays.*

A transformed cell, callus, tissue, or plant can be identified and isolated by selecting or screening the engineered plant material for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, quantitative real-time PCR, or reverse transcriptase PCR (RT-PCR) amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known. After a polynucleotide is stably incorporated into a transgenic plant, it can be introduced into other plants using, for example, standard breeding techniques.

Transgenic plants (or plant cells) can have an altered phenotype as compared to a corresponding control plant (or plant cell) that either lacks the transgene or does not express the transgene. A polypeptide can affect the phenotype of a plant (e.g., a transgenic plant) when expressed in the plant, e.g., at the appropriate time(s), in the appropriate tissue(s), or at the appropriate expression levels. Phenotypic effects can be evaluated relative to a control plant that does not express the exogenous polynucleotide of interest, such as a corresponding wild-type plant, a corresponding plant that is not transgenic for the exogenous polynucleotide of interest but otherwise is of the same genetic background as the transgenic plant of interest, or a corresponding plant of the same genetic background in which expression of the polypeptide is suppressed, inhibited, or not induced (e.g., where expression is under the control of an inducible promoter). A plant can be said "not to express" a polypeptide when the plant exhibits less than 10 percent (e.g., less than 9 percent, 8 percent, 7 percent, 6 percent, 5 percent, 4 percent, 3 percent, 2 percent, 1 percent, 0.5 percent, 0.1 percent, 0.01 percent, or 0.001 percent) of the amount of polypeptide or mRNA encoding the polypeptide exhibited by the plant of interest. Expression can be evaluated using methods including, for example, quantitative real-time PCR, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-specific or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

When a sugar-modulating polypeptide described herein is expressed in a plant, the transgenic plant can have an increased level of one or more sugars (e.g., glucose, fructose, or sucrose). For example, non-seed tissues of a transgenic plant can exhibit increased levels of one or more of glucose, fructose, and/or sucrose. The sugar level can be increased by at least 5 percent (e.g., 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 175, 200, 225, 250, 275, 300, 350, 400, 450, 500, 550, 600, 650, 700, 800, 900, or 1000 percent) as compared to the sugar level in a corresponding control plant that does not express the transgene. For example, a level of glucose, fructose, or sucrose in non-seed tissues of a plant can be increased by at least 7 percent to about 120 percent or any value therebetween, such as at least 9 percent, 10 percent, 11 percent, 15 percent, 18 percent, 20 percent, 21 percent, 22 percent, 24 percent, 27 percent, 29 percent, 30 percent, 31 percent, 35 percent, 36 percent, 37 percent, 40 percent, 43 percent, 50 percent, 51 percent, 60 percent, 63 percent, 70 percent, 75 percent, 80 percent, 90 percent, 105 percent, or 115 percent, as compared to the corresponding levels in a control plant. In some cases, a level of glucose in non-seed tissues of a plant can be increased by at least 10 percent to about 120 percent or any value therebetween, such as at least 15 percent, 18 percent, 21 percent, 24 percent, 27 percent, 29 percent, 31 percent, 35 percent, 37 percent, 40 percent, 43 percent, 50 percent, 60 percent, 70 percent, 75 percent, 80 percent, 90 percent, 105 percent, or 115 percent, as compared to the corresponding levels in a control plant. In some cases, a level of fructose in non-seed tissues of a plant can be increased by at least 7 percent to about 115 percent or any value therebetween, such as at least 10 percent, 15 percent, 18 percent, 20 percent, 24 percent, 30 percent, 36 percent, 40 percent, 44 percent, 50 percent, 55 percent, 60 percent, 70 percent, 75 percent, 80 percent, 90 percent, 105 percent, or 110 percent, as compared to the corresponding levels in a control plant. In other cases, a level of sucrose in non-seed tissues of a plant can be increased by at least 10 percent to about 100 percent or any value therebetween, such as at least 12 percent, 15 percent, 18 percent, 24 percent, 29 percent, 35 percent, 40 percent, 45 percent, 51 percent, 56 percent, 60 percent, 65 percent, 70 percent, 75 percent, 80 percent, 85 percent, 92 percent, or 97 percent, as compared to the corresponding levels in a control plant. In yet other cases, levels of glucose and fructose in non-seed tissues of a plant can be increased by at least 7 percent to about 120 percent or any value therebetween, such as at least 10 percent, 12 percent, 15 percent, 18 percent, 20 percent, 21 percent, 24 percent, 27 percent, 29 percent, 30 percent, 31 percent, 35 percent, 36 percent, 37 percent, 40 percent, 43 percent, 50 percent, 60 percent, 70 percent, 75 percent, 80 percent, 90 percent, 105 percent, or 115 percent, as compared to the corresponding levels in a control plant.

Seeds, Extracts, Non-Seed Tissues, Animal Feed, and Articles of Manufacture

Also provided herein are compositions such as food and feed products, and articles of manufacture, such as bags of seeds, based on transgenic plants described herein. Typically, a substantially uniform mixture of seeds is conditioned and bagged in packaging material by means known in the art to form an article of manufacture. Packaging material such as paper and cloth are well known in the art. Such a bag of seed preferably has a package label accompanying the bag, e.g., a tag or label secured to the packaging material, a label printed on the packaging material, or a label inserted within the bag. The package label may indicate that seed contained therein incorporates transgenes that provide increased amounts of one or more sugars in one or more tissues of plants grown from such seeds.

Seeds from transgenic plants described herein can be used as is, e.g., to grow plants, or can be used to make food products such as flours, vegetable oils, and insoluble fibers. Non-seed tissues from transgenic plants described herein can be used as is or can be used to make food products such as fresh, canned, and frozen fruits and vegetables. Seeds and non-seed tissues from transgenic plants described herein also can be used as animal feed. Transgenic plants described herein also can be used to make grains, such as wheat, oat, rice, barley, quinoa, and rye. Such products are useful to provide increased amounts of sugar(s) in the diet and to provide increased flavor.

Transgenic plants described herein can also serve as raw materials suitable for fermentation to produce ethanol. For example, corn cobs, corn stalks, sugarcane, sugarbeets, fruit (fresh or dried), citrus molasses, cane sorghum, and cotton can be fermented to produce ethyl alcohol. Fuel ethanol can also be manufactured using sugarcane juice or molasses as raw material. Producing ethanol from plant materials containing increased amounts of sugar can improve ethanol yields.

Transgenic plants described herein can also be used as a source from which to extract sugars, using techniques known in the art. For example, sugar can be extracted from sugarcane, sugarbeet, date palm, sorghum, and sugar maple. Molasses can also be extracted from sugarcane. The resulting extracts can be purified. Purified sugar, sugar syrup, sugar juice, or extracts containing sugar can be included in nutritional supplements as well as processed food products, e.g., soft drinks, sports drinks, ice cream, baked goods, relishes, sauces, tomato paste, canned foods, meats, salads, candy, fruit juices, vegetable juices, syrup, snack products, frozen entrees, breakfast cereals, breakfast bars, baby foods, and high fructose corn syrup. Sugar can also be included in cell culture media.

Methods

Also provided herein are methods that employ the described polynucleotides, polypeptides, plant cells, transgenic plants, seeds, and tissues. For example, a method of modulating the level of a sugar in a plant, such as non-seed tissue or seeds of a plant, is provided. The method includes introducing one or more exogenous nucleic acids described herein into a plant cell. A modulated level can be an increased level of a sugar, including one or more of glucose, fructose, and/or sucrose.

A method of producing a plant having a modulated sugar level (e.g., an increased glucose, fructose, and/or sucrose level) is also provided, which includes introducing into a plant cell one or more exogenous nucleic acids as previously described, and growing a plant from the plant cell. The increased level of one or more of glucose, fructose, and/or sucrose can be in the seed and/or the non-seed tissue of the plant.

A method of producing a sugar is also provided. The method includes extracting sugar from a transgenic plant (e.g., sugarcane or sugarbeet) described herein. Sugar can be extracted from such plants using techniques known in the art.

Transgenic plants (e.g., corn, wheat, and sugarbeets) having increased sugar levels can also be useful in lactate/lactic acid production processes. Lactate can be used to produce polylactide polymers (see, for example, U.S. Pat. No. 6,291,597). Furthermore, sugars can be useful in the production of polylactide polymers.

Finally, a method of producing ethanol is provided. The method includes fermentation of plant materials based on transgenic plants provided herein. Plant materials can be fermented to produce ethanol using techniques known in the art (see, for example, U.S. Pat. Nos. 6,509,180 and 6,927,048).

When the polynucleotides and polypeptides provided herein are expressed non-naturally (e.g., with respect to location in a plant, such as root vs. stem; environmental condition; plant species; time of development; and/or expression level), they can produce plants with modulated levels of sugars. These traits can be used to make use of or maximize plant products, including, without limitation, non-seed plant tissues, roots, seeds, flowers, fruits, extracts, and oils. For example, nucleic acids provided herein can be used to generate transgenic plants having increased expression of one or more polynucleotides involved in sugar synthesis. In some cases, nucleic acids provided herein can be used to generate transgenic plants having increased or decreased expression of one or more polypeptides involved in maintenance of sugar levels (e.g., regulation of sugar degradation). In some cases, nucleic acids provided herein can be used to generate transgenic plants having increased expression of one or more polypeptides involved in regulating expression of one or more genes involved in sugar synthesis or maintenance of sugar levels. Such transgenic plants may produce higher levels of one or more sugars (e.g., glucose, fructose, or sucrose), as discussed herein. Thus, the polynucleotides and polypeptides provided herein can be useful in the preparation of transgenic plants having particular application in the agricultural and nutritional industries.

The invention will be further described in the following examples, which do not limit the scope of the invention described in the claims.

EXAMPLES

Example 1

Transgenic Plants

The following symbols are used in the Examples: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

Ceres clone 625627 (SEQ ID NO:13) contains a nucleotide sequence that has homology to two different nucleotide sequences. The first 510 nucleotides at the 5' end correspond to a portion of an expressed sequence tag (GenBank accession number AW734757) from soybean that contains an AP2 DNA-binding domain. Nucleotides 505-725 correspond to a portion of a nucleic acid sequence that encodes an ATPase related protein. Ceres clone 625627 encodes a 174 amino acid polypeptide.

Ceres clone 32380 (SEQ ID NO:1) encodes a 232 amino acid polypeptide predicted to be a DNA-directed RNA polymerase II third largest subunit.

Ti plasmid vectors were constructed that contained Ceres clone 625627 or Ceres clone 32380 operably linked to the 35S promoter. The Ti plasmid vector used for these constructs, CRS338, contained a phosphinothricin acetyltransferase gene, which confers Finale™ resistance to transformed plants. Wild-type Arabidopsis Wassilewskija (Ws) plants were transformed separately with each Ti plasmid vector, essentially as described in Bechtold et al., *CR. Acad. Sci. Paris*, 316:1194-1199 (1993).

Arabidopsis lines containing Ceres clone 625627 or Ceres clone 32380 were designated ME02225 or ME05896, respectively. The presence of the Ceres clone 625627 vector in ME02225, and the Ceres clone 32380 vector in ME05896, was confirmed by Finale™ resistance, PCR amplification from green leaf tissue extract, and sequencing of PCR products. As controls, wild-type Arabidopsis Wassilewskija (Ws) plants were transformed with the empty vector SR00559.

Ten events of each of ME02225 and ME05896 were selected and screened for visible phenotypic alterations in the $T_1$ generation. The physical appearance of all $T_1$ plants was identical to that of the control plants.

Example 2

Analysis of Sugar Levels in ME02225 Events

Plants were grown from a mixture of seeds collected from $T_1$ events of ME02225. The plants were harvested ten days post-bolting. Non-seed tissues (e.g., aerial tissues) from four segregating Finale™-resistant $T_2$ plants were pooled and immediately frozen in liquid nitrogen. The tissues were stored at –80° C. and subsequently lyophilized for 72 hours. The freeze-dried tissues were crushed into a fine powder and prepared for analysis using gas chromatography-mass spectroscopy (GC-MS). Briefly, the freeze-dried tissues were extracted in triplicate using methanol, and then extracted using dichloromethane. The polar phases were derivatized using transmethylation, methoxyamination, and trimethylsylation. Derivatized extracts (2 µL) were injected into a Shimadzu GC-MS QP-2010 (Shimadzu Scientific Instruments, Columbia, Md.). The data were analyzed using the Shimadzu GC-MS Solutions software (Shimadzu Scientific Instruments). Briefly, target ion peak areas were integrated after identity confirmation using retention time standards and reference ion peak ratios. The target ion peak areas were normalized with respect to the internal standard and compared relative to the control sample. The normalized peak areas from glucose and fructose were averaged and the standard deviations were calculated.

Figure 5B:
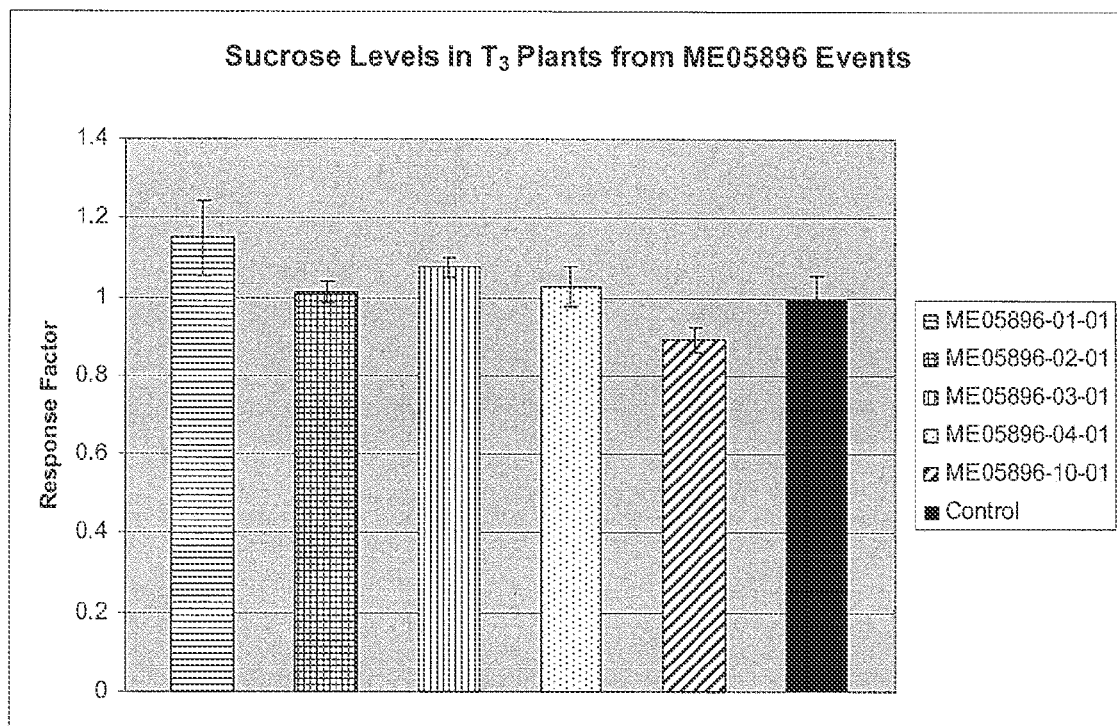
FIG. 5B is a graph plotting sucrose levels in $T_3$ plants from ME05896 events relative to control plants.

Non-seed tissues from $T_2$ plants of ME02225 had increased levels of glucose and fructose compared to the levels of glucose and fructose in non-seed tissues from corresponding control plants. As presented in FIG. 5, the levels of glucose and fructose were increased by 105% and 90%, respectively, in $T_2$ plants of ME02225 compared to the levels of glucose and fructose in the corresponding control plants.

In addition to analyzing ME02225 plants grown from a mixture of seeds, events of ME02225 were analyzed individually. Seeds from each of four events of ME02225 were planted separately. $T_2$ and $T_3$ plants from each of the four events of ME02225 were grown until ten days post-bolting. Non-seed tissues from four Finale™-resistant plants of each event were pooled, frozen in liquid nitrogen, and stored at –80° C. The frozen tissues were lyophilized for 72 hours and stored at –80° C. The freeze-dried tissues were crushed into a fine powder and prepared for analysis using GC-MS. Briefly, the lyophilized plant tissues were extracted in triplicate using methanol, and then extracted using dichloromethane. The polar phases were derivatized using methoxyamine and N-Methyl-N-(trimethylsilyl)trifluoroacetamide (MSTFA). Derivatized extracts were analyzed using GC-MS, and the data were analyzed as described above.

The GC-MS analysis showed that Finale™-resistant $T_2$ plants from events –02 and –04 had significantly increased glucose levels compared to control plants. As presented in Table 1, glucose levels were increased by 24% and 35% in events –02 and –04, respectively, compared to the corresponding control plants.

TABLE 1

Glucose levels (% Control) in $T_2$ and $T_3$ plants from ME02225 events

| | Ws Control | ME02225-02 | ME02225-03 | ME02225-04 | ME02225-05 |
|---|---|---|---|---|---|
| $T_2$ | 100 ± 12 | 124 ± 3 | 109 ± 21 | 135 ± 8 | 77 ± 3 |
| p-value | NA | 0.07 | 0.56 | 0.02 | 0.08 |
| $T_3$ | 100 ± 12 | 137 ± 6 | 108 ± 7 | 129 ± 11 | 103 ± 4 |
| p-value | NA | <0.01 | 0.28 | 0.02 | 0.61 |

Levels of glucose in Finale™-resistant $T_3$ plants from four ME02225 events also were analyzed using GC-MS. Events –02 and –04 had significantly increased glucose levels compared to control plants. As presented in Table 1, glucose levels were increased by 37% and 29% in events –02 and –04, respectively, compared to the corresponding control plants.

The GC-MS analysis also showed that Finale™-resistant T$_2$ plants from events –02 and –04 had significantly increased fructose levels compared to control plants. As presented in Table 2, fructose levels were increased by 10% and 30% in events –02 and –04, respectively, compared to the corresponding control plants. The 10% increase in fructose level in event –02 was not statistically significant.

TABLE 2

Fructose levels (% Control) in T$_2$ and T$_3$ plants from ME02225 events

|  | Ws Control | ME02225-02 | ME02225-03 | ME02225-04 | ME02225-05 |
|---|---|---|---|---|---|
| T$_2$ | 100 ± 17 | 110 ± 8 | 101 ± 15 | 130 ± 6 | 70 ± 6 |
| p-value | NA | 0.41 | 0.92 | 0.08 | 0.08 |
| T$_3$ | 100 ± 13 | 140 ± 10 | 110 ± 12 | 130 ± 10 | 100 ± 9 |
| p-value | NA | <0.01 | 0.45 | <0.01 | <0.01 |

Levels of fructose in Finale™-resistant T$_3$ plants from four ME02225 events also were analyzed using GC-MS. Events –02 and –04 had significantly increased fructose levels compared to control plants. As presented in Table 2, fructose levels were increased by 40% and 30% in events –02 and –04, respectively, compared to the corresponding control plants.

There were no observable or statistically significant differences between T$_2$ ME02225 and control plants in germination, onset of flowering, rosette diameter, fertility, plant height, and general morphology/architecture.

Example 3

Analysis of Sugar Levels in ME05896 Events

Levels of sucrose in Finale™-resistant T$_2$ plants from five ME05896 events were analyzed using GC-MS, as described above. As presented in Table 3, sucrose levels were increased by 63% and 22% in events –01 and –02, respectively, compared to the corresponding control plants.

Levels of sucrose in Finale™-resistant T$_3$ plants from five ME05896 events also were analyzed using GC-MS. As presented in Table 3, the trend of increased sugar level exhibited by T$_3$ plants of ME05896 is similar to that exhibited by the T$_2$ plants, particularly in the case of event –01. The results also are presented in FIG. 5B.

TABLE 3

Sucrose levels (fold increase) in T$_2$ plants from ME05896 events

|  | ME05896-01 | ME05896-02 | ME05896-03 | ME05896-04 | ME05896-10 | Control |
|---|---|---|---|---|---|---|
| T$_2$ | 1.63 ± 0.12 | 1.22 ± 0.07 | 1.07 ± 0.04 | 1.01 ± 0.08 | 1.07 ± 0.08 | 1.00 ± 0.13 |
| p-value | <0.01 | 0.08 | 0.40 | 0.90 | 0.48 | NA |
| T$_3$ | 1.14 ± 0.09 | 1.01 ± 0.03 | 1.07 ± 0.03 | 1.02 ± 0.05 | 0.89 ± 0.03 | 1.00 ± 0.06 |
| p-value | 0.10 | 0.40 | 0.01 | 0.40 | 0.01 | NA |

Example 4

Determination of Functional Homolog and/or Ortholog Sequences

A subject sequence was considered a functional homolog and/or ortholog of a query sequence if the subject sequence encoded a protein having a function and/or activity similar to the protein encoded by the query sequence. A process known as Reciprocal BLAST (Rivera et al., *Proc. Natl. Acad. Sci. (U.S.A.)*, 1998, 95:6239-6244) was used to identify potential functional homolog and/or ortholog sequences from available databases of public and proprietary peptide sequences, including the NCBI NR protein database and a private Ceres database of peptide translations of sequences from Ceres clones.

Before starting a Reciprocal BLAST process, BLAST was used to search a specific query polypeptide against all polypeptides from its source species in order to identify polypeptides having 80% or greater sequence identity with the query polypeptide. The query polypeptide together with polypeptides identified as having 80% or greater sequence identity with the query polypeptide were designated as a cluster.

The main Reciprocal BLAST process consists of two rounds of BLAST searches: a forward search and a reverse search. In the forward search step, a query polypeptide sequence, "polypeptide A," from source species SA was BLASTed against all protein sequences from a species of interest. The best matches, or top hits, were determined using an E-value cutoff of $10^{-5}$ and an identity cutoff of 35%. Among the top hits, the hit with the lowest E-value was considered the best hit and a potential functional homolog and/or ortholog. Any other top hit(s) having 80% or greater sequence identity with the best hit or the original query polypeptide was also considered a potential functional homolog and/or ortholog. This process was repeated for all species of interest.

In the reverse search of the Reciprocal Blast process, the top hits identified in the forward search, from all species, were BLASTed against all protein sequences from the source species SA. A top hit from the forward search that returned a polypeptide from the aforementioned cluster as its best hit was also considered a potential functional homolog and/or ortholog.

Manual inspection of potential functional homologs and/or orthologs was carried out to select identified functional homologs and/or orthologs. The results are presented in FIG. 6. Percent identities to SEQ ID NO:2 are shown in Table 4 below.

| Designation | Species | SEQ ID NO: | % Identity |
|---|---|---|---|
| CeresClone 32380 | *Arabidopsis thaliana* | 2 | 100.00 |
| gi\|21593370 | *Arabidopsis thaliana* | 3 | 86.80 |

-continued

| Designation | Species | SEQ ID NO: | % Identity |
|---|---|---|---|
| CeresClone 692249 | *Glycine max* | 4 | 76.40 |
| CeresClone 244359 | *Zea mays* | 6 | 73.50 |
| gi\|50898416 | *Oryza sativa* subsp. *japonica* | 7 | 72.40 |
| CeresClone 698259 | *Triticum aestivum* | 5 | 70.10 |
| gi\|21593370T | *Arabidopsis thaliana* | 8 | 87.00 |
| CeresClone692249T | *Glycine max* | 9 | 76.02 |
| CeresClone244359T | *Zea mays* | 11 | 70.00 |

-continued

| Designation | Species | SEQ ID NO: | % Identity |
|---|---|---|---|
| gi\|50898416T | *Oryza sativa* subsp. *japonica* | 12 | 68.97 |
| CeresClone 698259T | *Triticum aestivum* | 10 | 66.52 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of modulating the level of a sugar in a plant, said method comprising a) introducing into a plurality of plant cells an isolated nucleic acid comprising a nucleic acid sequence encoding a polypeptide having 95 percent or greater sequence identity to an amino acid sequence set forth in SEQ ID NO:2; and b) selecting a plant produced from said plurality of plant cells that has a different sugar level as compared to a sugar level in a corresponding control plant that does not comprise said isolated nucleic acid.

2. A method of modulating the level of a sugar in a plant, said method comprising introducing into a plant cell (a) a first isolated nucleic acid comprising a nucleic acid sequence encoding a polypeptide having 95 percent or greater sequence identity to the amino acid sequence set forth in SEQ ID NO:2; and (b) a second isolated nucleic acid comprising a nucleic acid sequence encoding a polypeptide having 95% percent or greater sequence identity to an amino acid sequence set forth in SEQ ID NO:14; wherein a plant produced from said plant cell has a different sugar level as compared to a sugar level in a corresponding control plant that does not comprise said first isolated nucleic acid or said second isolated nucleic acid.

3. The method of claim 1, wherein said different sugar level is an increased level of one or more sugars.

4. A method of producing a plant having a modulated level of a sugar, said method comprising (a) introducing into a plurality of plant cells an isolated nucleic acid comprising a nucleic acid sequence encoding a polypeptide having 95 percent or greater sequence identity to an amino acid sequence set forth in SEQ ID NO:2; (b) selecting a plant produced from said plurality of plant cells that has a different sugar level as compared to a sugar level in a corresponding control plant that does not comprise said isolated nucleic acid; and (c) growing said plant.

5. A method of producing a plant having a modulated level of a sugar, said method comprising (a) introducing into a plant cell a first isolated nucleic acid comprising a nucleic acid sequence encoding a polypeptide having 95 percent or greater sequence identity to an amino acid sequence set forth in SEQ ID NO:2, and a second isolated nucleic acid comprising a nucleic acid sequence encoding a polypeptide having 95 percent or greater sequence identity to an amino acid sequence corresponding to SEQ ID NO:14; and (b) growing a plant from said plant cell.

6. The method of claim 4, wherein said modulated level is an increased level of one or more sugars.

7. The method of claim 1, wherein said isolated nucleic acid is operably linked to a regulatory region.

8. The method of claim 2, wherein said first isolated nucleic acid and said second isolated nucleic acid are each operably linked to a regulatory region.

9. The method of claim 7, wherein said regulatory region is a promoter.

10. The method of claim 2, wherein said different sugar level is an increased level of one or more sugars.

11. The method of claim 5, wherein said modulated level is an increased level of one or more sugars.

12. The method of claim 8, wherein said regulatory region is a promoter.

13. The method of claim 4, wherein said isolated nucleic acid is operably linked to a regulatory region.

14. The method of claim 13, wherein said regulatory region is a promoter.

15. The method of claim 5, wherein said first isolated nucleic acid and said second isolated nucleic acid are each operably linked to a regulatory region.

16. The method of claim 15, wherein said regulatory region is a promoter.

17. A plant comprising an exogenous nucleic acid, said exogenous nucleic acid comprising a nucleotide sequence encoding a encoding a polypeptide having 95 percent or greater sequence identity to an amino acid sequence set forth in SEQ ID NO:2, wherein said plant has a sucrose content that is increased at least 7% as compared to the sucrose content in a corresponding control plant that does not comprise said exogenous nucleic acid.

18. The plant of claim 17, wherein said exogenous nucleic acid is operably linked to a regulatory region.

19. The plant of claim 18, wherein said regulatory region is a promoter.

20. A plant comprising (a) a first exogenous nucleic acid comprising a nucleic acid sequence encoding a polypeptide having 95 percent or greater sequence identity to an amino acid sequence set forth in SEQ ID NO:2; and (b) a second exogenous nucleic acid comprising a nucleic acid sequence encoding a polypeptide having 95 percent or greater sequence identity to an amino acid sequence corresponding to SEQ ID NO:14; wherein said plant has a different sugar level as compared to a sugar level in a corresponding control plant that does not comprise said first exogenous nucleic acid or said second exogenous nucleic acid.

21. The plant of claim 20, wherein said different sugar level is an increased level of one or more sugars.

22. The plant of claim 20, wherein said wherein said first exogenous nucleic acid and said second exogenous nucleic acid is operably linked to a regulatory region.

23. The plant of claim 22, wherein said regulatory region is a promoter.

* * * * *

UNITED STATES PATENT AND TRADEMARK OFFICE
CERTIFICATE OF CORRECTION

PATENT NO.         : 8,076,535 B2  
APPLICATION NO.    : 12/256761  
DATED              : December 13, 2011  
INVENTOR(S)        : Boris Jankowski, Kenneth A. Feldmann and Steven Craig Bobzin Page 1 of 1

It is certified that error appears in the above-identified patent and that said Letters Patent is hereby corrected as shown below:

Column 59, line 32, Claim 2, delete "95% percent" and insert --95 percent--, therefor.

Column 60, line 36, Claim 17, before "polypeptide" delete "encoding a".

Column 60, line 58, Claim 22, after "said" delete "wherein said".

Column 60, line 60, Claim 22, delete "is" and insert --are each--, therefor.

Signed and Sealed this  
Tenth Day of July, 2012

David J. Kappos  
*Director of the United States Patent and Trademark Office*

SEQUENCE LISTING

```
<160> NUMBER OF SEQ ID NOS: 14

<210> SEQ ID NO 1
<211> LENGTH: 922
<212> TYPE: DNA
<213> ORGANISM: Arabidopsis thaliana
<220> FEATURE:
<221> NAME/KEY: misc_feature
<222> LOCATION: (1)..(922)
<223> OTHER INFORMATION: Ceres CLONE ID no. 32380
<220> FEATURE:
<221> NAME/KEY: CDS
<222> LOCATION: (90)..(786)
<223> OTHER INFORMATION: Referenced by SEQ ID NO: 2

<400> SEQUENCE: 1
ctctccaaat ttcttcttct tctccggcga agaaatcgaa aagtcattac cctaagagtc      60
ccagagtcgt cagaaggaac agcttttgaa atggacggtg tcacatacca aagattccca    120
acggtgaaga tccgtgagct taaagatgac tacgccaagt tcgagcttcg tgaaaccgac    180
gtttcaatgg ccaacgctct ccgtcgcgta atgatctccg aagtccccac catggcaatc    240
catctcgtca aaatcgaggt taattcctct gttctcaacg acgagttcat tgctcaacga    300
cttcgtctca tccctctcac tagcgagcgt gctatgagca tgcggttctg tcaagattgt    360
gaagattgta acggagatga acattgcgag ttctgctctg ttgagtttcc ccttagtgct    420
aagtgtgtta ctgaccaaac cctagatgtt actagtaggg atctctacag tgctgatcct    480
actgttactc ctgttgattt cactagtaac tcatctactt ctgattcaag cgagcacaag    540
ggaattatca ttgcgaaact acgcagggga caagagttga agcttaaagc attagcgagg    600
aaaggaattg ggaaagatca tgcgaaatgg tctcctgcag ctactgttac gtatatgtat    660
gagcctgaca ttattatcaa tgaagagatg atgaacactt tgacagatga ggaaaaaatt    720
gacttgattg agagcagtcc taccaaagtg tttggcatta ccgacaggt taatttcgat    780 gttctgtaag aataacatct atacaagttt atagctttga gacttcaata tgattgtact    840
actttatagg ctaccatgct ttgaaatata tgtatgtgat gtggtgtatg aattttcttt    900
aagtgtttag tgcgtttagc cc                                              922

<210> SEQ ID NO 2
<211> LENGTH: 232
<212> TYPE: PRT
<213> ORGANISM: Arabidopsis thaliana
<220> FEATURE:
<221> NAME/KEY: misc_feature
<222> LOCATION: (16)..(130)
<223> OTHER INFORMATION: Pfam Name: RNA_pol_L; Pfam Description: RNA
      polymerase Rpb3/Rpb11 dimerisation domain
<220> FEATURE:
<221> NAME/KEY: misc_feature
<222> LOCATION: (53)..(181)
<223> OTHER INFORMATION: Pfam Name: RNA_pol_A_bac; Pfam Description: RNA
      polymerase Rpb3/RpoA insert domain

<400> SEQUENCE: 2
```

```
Met Asp Gly Val Thr Tyr Gln Arg Phe Pro Thr Val Lys Ile Arg Glu
1               5                   10                  15

Leu Lys Asp Asp Tyr Ala Lys Phe Glu Leu Arg Glu Thr Asp Val Ser
            20                  25                  30

Met Ala Asn Ala Leu Arg Arg Val Met Ile Ser Glu Val Pro Thr Met
        35                  40                  45

Ala Ile His Leu Val Lys Ile Glu Val Asn Ser Ser Val Leu Asn Asp
    50                  55                  60

Glu Phe Ile Ala Gln Arg Leu Arg Leu Ile Pro Leu Thr Ser Glu Arg
65                  70                  75                  80

Ala Met Ser Met Arg Phe Cys Gln Asp Cys Glu Asp Cys Asn Gly Asp
                85                  90                  95

Glu His Cys Glu Phe Cys Ser Val Glu Phe Pro Leu Ser Ala Lys Cys
            100                 105                 110

Val Thr Asp Gln Thr Leu Asp Val Thr Ser Arg Asp Leu Tyr Ser Ala
        115                 120                 125

Asp Pro Thr Val Thr Pro Val Asp Phe Thr Ser Asn Ser Ser Thr Ser
    130                 135                 140

Asp Ser Ser Glu His Lys Gly Ile Ile Ile Ala Lys Leu Arg Arg Gly
145                 150                 155                 160

Gln Glu Leu Lys Leu Lys Ala Leu Ala Arg Lys Gly Ile Gly Lys Asp
                165                 170                 175

His Ala Lys Trp Ser Pro Ala Ala Thr Val Thr Tyr Met Tyr Glu Pro
            180                 185                 190

Asp Ile Ile Ile Asn Glu Glu Met Met Asn Thr Leu Thr Asp Glu Glu
        195                 200                 205

Lys Ile Asp Leu Ile Glu Ser Ser Pro Thr Lys Val Phe Gly Ile Thr
    210                 215                 220

Gly Gln Val Asn Phe Asp Val Leu

<210> SEQ ID NO 3
<211> LENGTH: 319
<212> TYPE: PRT
<213> ORGANISM: Arabidopsis thaliana
<220> FEATURE:
<221> NAME/KEY: misc_feature
<222> LOCATION: (1)..(319)
<223> OTHER INFORMATION: Public GI no. 21593370

<400> SEQUENCE: 3

Met Asp Gly Ala Thr Tyr Gln Arg Phe Pro Lys Ile Lys Ile Arg Glu
1               5                   10                  15

Leu Lys Asp Asp Tyr Ala Lys Phe Glu Leu Arg Glu Thr Asp Val Ser
            20                  25                  30

Met Ala Asn Ala Leu Arg Arg Val Met Ile Ser Glu Val Pro Thr Val
        35                  40                  45

Ala Ile Asp Leu Val Glu Ile Glu Val Asn Ser Ser Val Leu Asn Asp
    50                  55                  60

Glu Phe Ile Ala His Arg Leu Gly Leu Ile Ser Leu Thr Ser Glu Arg
65                  70                  75                  80

Ala Met Ser Met Arg Phe Ser Arg Asp Cys Asp Ala Cys Asp Gly Asp
                85                  90                  95

Gly Gln Cys Glu Phe Cys Ser Val Glu Phe Arg Leu Ser Ser Lys Cys
            100                 105                 110

Val Thr Asp Gln Thr Leu Asp Val Thr Ser Arg Asp Leu Tyr Ser Ala
        115                 120                 125
```

```
Asp Pro Thr Val Thr Pro Val Asp Phe Thr Ile Asp Ser Ser Val Ser
        130                 135                 140

Asp Ser Ser Glu His Lys Gly Ile Ile Ile Val Lys Leu Arg Arg Gly
145                 150                 155                 160

Gln Glu Leu Lys Leu Arg Ala Ile Ala Arg Lys Gly Ile Gly Lys Asp
                165                 170                 175

His Ala Lys Trp Ser Pro Ala Ala Thr Val Thr Phe Met Tyr Glu Pro
            180                 185                 190

Asp Ile Ile Ile Asn Glu Asp Met Met Asp Thr Leu Ser Asp Glu Glu
        195                 200                 205

Lys Ile Asp Leu Ile Glu Ser Ser Pro Thr Lys Val Phe Gly Met Asp
210                 215                 220

Pro Val Thr Arg Gln Val Val Val Asp Pro Glu Ala Tyr Thr Tyr
225                 230                 235                 240

Asp Glu Glu Val Ile Lys Lys Ala Glu Ala Met Gly Lys Pro Gly Leu
                245                 250                 255

Ile Glu Ile Ser Pro Lys Asp Asp Ser Phe Ile Phe Thr Val Glu Ser
            260                 265                 270

Thr Gly Ala Val Lys Ala Ser Gln Leu Val Leu Asn Ala Ile Asp Leu
        275                 280                 285

Leu Lys Gln Lys Leu Asp Ala Val Arg Leu Ser Asp Asp Thr Val Glu
290                 295                 300

Ala Asp Asp Gln Phe Gly Glu Leu Gly Ala His Met Arg Gly Gly
305                 310                 315

<210> SEQ ID NO 4
<211> LENGTH: 319
<212> TYPE: PRT
<213> ORGANISM: Glycine max
<220> FEATURE:
<221> NAME/KEY: misc_feature
<222> LOCATION: (1)..(319)
<223> OTHER INFORMATION: Ceres CLONE ID no. 692249

<400> SEQUENCE: 4

Met Glu Gly Gly Val Ser Tyr Ala Arg Met Pro Arg Val Lys Ile Arg
1               5                   10                  15

Glu Leu Lys Asp Asp Tyr Ala Lys Phe Glu Leu Arg Asp Thr Asp Ala
                20                  25                  30

Ser Ile Ala Asn Ala Leu Arg Arg Val Met Ile Ala Glu Val Pro Thr
            35                  40                  45

Val Ala Ile Asp Leu Val Glu Ile Glu Val Asn Ser Ser Val Leu Asn
        50                  55                  60

Asp Glu Phe Ile Ala His Arg Leu Gly Leu Ile Pro Leu Thr Ser Glu
65                  70                  75                  80

Arg Ala Met Ser Met Arg Phe Ser Arg Asp Cys Asp Ala Cys Asp Gly
                85                  90                  95

Asp Gly Gln Cys Glu Phe Cys Ser Val Glu Phe His Leu Arg Val Lys
            100                 105                 110

Cys Met Thr Asp Gln Thr Leu Asp Val Thr Ser Lys Asp Leu Tyr Ser
        115                 120                 125

Ser Asp Pro Thr Val Ser Pro Val Asp Phe Ser Asp Pro Ser Ala Thr
130                 135                 140

Asp Ser Asp Asn Asn Arg Gly Ile Ile Ile Val Lys Leu Arg Arg Gly
145                 150                 155                 160

Gln Glu Leu Lys Leu Arg Ala Ile Ala Arg Lys Gly Ile Gly Lys Asp
                165                 170                 175
```

```
                          165                 170                 175
His Ala Lys Trp Ser Pro Ala Ala Thr Val Thr Phe Met Tyr Glu Pro
            180                 185                 190

Glu Ile His Ile Asn Glu Asp Leu Met Glu Thr Leu Thr Leu Glu Glu
            195                 200                 205

Lys Arg Glu Trp Val Asp Ser Ser Pro Thr Arg Val Phe Glu Ile Asp
            210                 215                 220

Pro Val Thr Gln Gln Val Met Val Val Asp Ala Glu Ala Tyr Thr Tyr
225                 230                 235                 240

Asp Asp Glu Val Leu Lys Lys Ala Glu Ala Met Gly Lys Pro Gly Leu
                245                 250                 255

Val Glu Ile Ile Ala Arg Gln Asp Ser Phe Ile Phe Thr Val Glu Ser
                260                 265                 270

Thr Gly Ala Val Lys Ala Ser Gln Leu Val Leu Asn Ala Ile Glu Ile
                275                 280                 285

Leu Lys Gln Lys Leu Asp Ala Val Arg Leu Ser Glu Asp Thr Val Glu
                290                 295                 300

Ala Asp Asp Gln Phe Gly Glu Leu Gly Ala His Met Arg Gly Gly
305                 310                 315

<210> SEQ ID NO 5
<211> LENGTH: 331
<212> TYPE: PRT
<213> ORGANISM: Triticum aestivum
<220> FEATURE:
<221> NAME/KEY: misc_feature
<222> LOCATION: (1)..(331)
<223> OTHER INFORMATION: Ceres CLONE ID no. 698259

<400> SEQUENCE: 5

Met Glu Arg Ser Ala Ala Gly Ala Ser Tyr Gln Arg Phe Pro Arg Val
1               5                   10                  15

Arg Ile Arg Glu Leu Lys Asp Glu Tyr Ala Lys Phe Glu Leu Lys Asp
                20                  25                  30

Thr Asp Ala Ser Met Ala Asn Ala Leu Arg Arg Val Met Ile Ala Glu
            35                  40                  45

Val Pro Thr Val Ala Ile Asp Leu Val Glu Ile Glu Ser Asn Ser Ser
    50                  55                  60

Val Leu Asn Asp Glu Phe Leu Ala His Arg Leu Gly Leu Ile Pro Leu
65                  70                  75                  80

Thr Ser Ser Ala Ala Met Ser Met Arg Phe Ser Arg Asp Cys Asp Ala
                85                  90                  95

Cys Asp Gly Asp Gly Ser Cys Glu Tyr Cys Ser Val Glu Phe His Leu
            100                 105                 110

Ala Ala Arg Ala Thr Asp Ser Gly Gln Thr Leu Glu Val Thr Ser Thr
        115                 120                 125

Lys Asp Leu Arg Ser Thr Asp Pro Lys Val Cys Pro Val Asp Gln Gln
    130                 135                 140

Arg Glu Tyr Gln Gln Ala Leu Gly Asn Val Asp Ala Tyr Glu Pro Asp
145                 150                 155                 160

Ala Ala Gly Asp His Arg Gly Ile Leu Ile Val Lys Leu Arg Gly
                165                 170                 175

Gln Glu Leu Arg Leu Arg Ala Ile Ala Arg Lys Gly Ile Gly Lys Asp
            180                 185                 190

His Ala Lys Trp Ser Pro Ala Ala Thr Val Thr Phe Met Tyr Glu Pro
            195                 200                 205
```

-continued

Asp Ile Arg Ile Asn Gln Glu Leu Met Glu Thr Leu Thr Leu Glu Glu
210                 215                 220

Lys Gln Ser Trp Val Glu Ser Pro Thr Lys Val Phe Asp Ile Asp
225                 230                 235                 240

Pro Val Thr Gln Gln Val Thr Ile Val Asp Pro Glu Ala Tyr Thr Tyr
            245                 250                 255

Asp Asp Glu Val Ile Lys Lys Ala Glu Ala Met Gly Lys Pro Gly Leu
                260                 265                 270

Val Glu Ile Asn Ala Lys Glu Asp Ser Phe Val Phe Thr Val Glu Thr
        275                 280                 285

Thr Gly Ala Ile Thr Ala Tyr Glu Leu Ile Met Asn Ala Ile Thr Val
    290                 295                 300

Leu Arg Gln Lys Leu Asp Ala Val Arg Leu Gln Asp Asp Gly Asp
305                 310                 315                 320

Leu Gly Glu Leu Gly Ala His Leu Ile Gly Gly
                325                 330

<210> SEQ ID NO 6
<211> LENGTH: 328
<212> TYPE: PRT
<213> ORGANISM: Zea mays
<220> FEATURE:
<221> NAME/KEY: misc_feature
<222> LOCATION: (1)..(328)
<223> OTHER INFORMATION: Ceres CLONE ID no. 244359

<400> SEQUENCE: 6

Met Asp Arg Pro Ser Gly Thr Ser Tyr Gln Arg Phe Pro Arg Val Arg
1               5                   10                  15

Ile Arg Glu Leu Lys Asp Asp Tyr Ala Lys Phe Glu Leu Arg Asp Thr
            20                  25                  30

Asp Ala Ser Met Ala Asn Ala Leu Arg Arg Val Met Ile Ala Glu Val
        35                  40                  45

Pro Thr Val Ala Ile Asp Leu Val Glu Ile Glu Val Asn Ser Ser Val
    50                  55                  60

Leu Asn Asp Glu Phe Ile Ala His Arg Leu Gly Leu Ile Pro Leu Thr
65                  70                  75                  80

Ser Ala Ala Ala Met Gln Met Arg Phe Ser Arg Asp Cys Asp Ala Cys
                85                  90                  95

Asp Gly Asp Gly Ser Cys Glu Tyr Cys Ser Val Glu Phe His Leu Ser
            100                 105                 110

Val His Ala Thr Asp Ser Asp Gln Thr Leu Glu Val Thr Ser Asn Asp
        115                 120                 125

Leu Arg Ser Met Asp Pro Lys Val Cys Pro Val Asp Gln Ala Arg Ala
    130                 135                 140

Tyr Gln His Ala Leu Gly Gly Thr Asp Pro Phe Gly Ala Asn Ala Ser
145                 150                 155                 160

Asn Glu Asn Arg Gly Ile Leu Ile Val Lys Leu Arg Arg Gly Gln Glu
                165                 170                 175

Leu Arg Leu Arg Ala Ile Ala Arg Lys Gly Ile Gly Lys Asp His Ala
            180                 185                 190

Lys Trp Ser Pro Ala Ala Thr Val Thr Phe Met Tyr Glu Pro Asp Ile
        195                 200                 205

Arg Ile Asn Glu Glu Leu Met Glu Thr Leu Thr Val Glu Glu Arg Ile
    210                 215                 220

Ser Leu Ile Glu Ser Ser Pro Thr Lys Val Phe Glu Leu Asp Ser Ala
225                 230                 235                 240

```
Asn Gln Val Val Lys Asn Ala Glu Ala Tyr Thr Tyr Asp Asp Glu
            245                 250                 255

Val Ile Lys His Ala Glu Ala Ile Gly Lys Pro Gly Leu Val Glu Ile
        260                 265                 270

Thr Ala Lys Glu Asp Ser Phe Val Phe Thr Val Glu Thr Thr Gly Ala
        275                 280                 285

Ile Thr Ala Tyr Glu Leu Ile Met Asn Ala Ile Thr Val Leu Arg Gln
        290                 295                 300

Lys Leu Asp Ala Val Arg Leu Gln Asp Asp Gly Asp Leu Gly Glu
305                 310                 315                 320

Leu Gly Ala His Leu Gly Gly Pro
                325

<210> SEQ ID NO 7
<211> LENGTH: 330
<212> TYPE: PRT
<213> ORGANISM: Oryza sativa
<220> FEATURE:
<221> NAME/KEY: misc_feature
<222> LOCATION: (1)..(330)
<223> OTHER INFORMATION: Public GI no. 50898416

<400> SEQUENCE: 7

Met Glu Arg Ala Ala Gly Gly Val Ser Tyr Gln Arg Phe Pro Arg Val
1               5                   10                  15

Arg Ile Arg Glu Leu Lys Asp Asp Tyr Ala Lys Phe Glu Leu Arg Asp
            20                  25                  30

Thr Asp Ala Ser Met Ala Asn Ala Leu Arg Arg Val Met Ile Ala Glu
        35                  40                  45

Val Pro Thr Val Ala Ile Asp Leu Val Glu Ile Glu Val Asn Ser Ser
    50                  55                  60

Val Leu Asn Asp Glu Phe Ile Ala His Arg Leu Gly Leu Ile Pro Leu
65                  70                  75                  80

Thr Ser Ala Ala Ala Met Ala Met Arg Phe Ser Arg Asp Cys Asp Ala
                85                  90                  95

Cys Asp Gly Asp Gly Ser Cys Glu Tyr Cys Ser Val Glu Phe His Leu
            100                 105                 110

Ala Ala Arg Ala Thr Asp Ser Asp Gln Thr Leu Glu Val Thr Ser Asn
        115                 120                 125

Asp Leu Arg Ser Thr Asp Pro Lys Val Cys Pro Val Asp Gln Ala Arg
    130                 135                 140

Ala Tyr Gln His Ala Leu Gly Gly Thr Glu Pro Phe Asp Thr Ala Ala
145                 150                 155                 160

Ala Ala Asp Gln Arg Gly Ile Leu Ile Val Lys Leu Arg Arg Gly Gln
                165                 170                 175

Glu Leu Arg Leu Arg Ala Ile Ala Arg Lys Gly Ile Gly Lys Asp His
            180                 185                 190

Ala Lys Trp Ser Pro Ala Ala Thr Val Thr Phe Met Tyr Glu Pro Glu
        195                 200                 205

Ile Arg Ile Asn Glu Glu Leu Met Glu Thr Leu Thr Leu Glu Glu Lys
    210                 215                 220

Arg Asn Leu Val Glu Ser Ser Pro Thr Lys Val Phe Asn Ile Asp Pro
225                 230                 235                 240

Asn Thr Gln Gln Val Val Val Glu Asp Ala Glu Ala Tyr Thr Tyr Asp
                245                 250                 255

Asp Glu Val Ile Lys Lys Ala Asp Ala Met Gly Lys Pro Gly Leu Ile
```

```
                    260                 265                 270
Glu Ile Asn Ala Lys Glu Asp Ser Phe Ile Phe Thr Val Glu Thr Thr
                275                 280                 285
Gly Ala Ile Thr Ala Tyr Glu Leu Ile Met Asn Ala Ile Thr Val Leu
            290                 295                 300
Arg Gln Lys Leu Asp Ala Val Arg Leu Gln Asp Asp Ala Asp Leu
305                 310                 315                 320
Gly Glu Leu Gly Ala His Leu Val Gly Gly
                325                 330

<210> SEQ ID NO 8
<211> LENGTH: 226
<212> TYPE: PRT
<213> ORGANISM: Zea mays
<220> FEATURE:
<221> NAME/KEY: misc_feature
<222> LOCATION: (1)..(226)
<223> OTHER INFORMATION: Public GI no. 21593370T
<220> FEATURE:
<221> NAME/KEY: misc_feature
<222> LOCATION: (1)..(226)
<223> OTHER INFORMATION: Truncated portion of Public GI no. 21593370

<400> SEQUENCE: 8

Met Asp Gly Ala Thr Tyr Gln Arg Phe Pro Lys Ile Lys Ile Arg Glu
1               5                   10                  15
Leu Lys Asp Asp Tyr Ala Lys Phe Glu Leu Arg Glu Thr Asp Val Ser
            20                  25                  30
Met Ala Asn Ala Leu Arg Arg Val Met Ile Ser Glu Val Pro Thr Val
        35                  40                  45
Ala Ile Asp Leu Val Glu Ile Glu Val Asn Ser Ser Val Leu Asn Asp
    50                  55                  60
Glu Phe Ile Ala His Arg Leu Gly Leu Ile Ser Leu Thr Ser Glu Arg
65                  70                  75                  80
Ala Met Ser Met Arg Phe Ser Arg Asp Cys Asp Ala Cys Asp Gly Asp
                85                  90                  95
Gly Gln Cys Glu Phe Cys Ser Val Glu Phe Arg Leu Ser Ser Lys Cys
            100                 105                 110
Val Thr Asp Gln Thr Leu Asp Val Thr Ser Arg Asp Leu Tyr Ser Ala
        115                 120                 125
Asp Pro Thr Val Thr Pro Val Asp Phe Thr Ile Asp Ser Ser Val Ser
    130                 135                 140
Asp Ser Ser Glu His Lys Gly Ile Ile Val Lys Leu Arg Arg Gly
145                 150                 155                 160
Gln Glu Leu Lys Leu Arg Ala Ile Ala Arg Lys Gly Ile Gly Lys Asp
                165                 170                 175
His Ala Lys Trp Ser Pro Ala Ala Thr Val Thr Phe Met Tyr Glu Pro
            180                 185                 190
Asp Ile Ile Ile Asn Glu Asp Met Met Asp Thr Leu Ser Asp Glu Glu
        195                 200                 205
Lys Ile Asp Leu Ile Glu Ser Ser Pro Thr Lys Val Phe Gly Met Asp
    210                 215                 220
Pro Val
225

<210> SEQ ID NO 9
<211> LENGTH: 226
<212> TYPE: PRT
<213> ORGANISM: Zea mays
```

-continued

```
<220> FEATURE:
<221> NAME/KEY: misc_feature
<222> LOCATION: (1)..(226)
<223> OTHER INFORMATION: Ceres CLONE ID no. 692249T
<220> FEATURE:
<221> NAME/KEY: misc_feature
<222> LOCATION: (1)..(226)
<223> OTHER INFORMATION: Truncated portion of Ceres CLONE ID no. 692249

<400> SEQUENCE: 9

Met Glu Gly Gly Val Ser Tyr Ala Arg Met Pro Arg Val Lys Ile Arg
1               5                   10                  15

Glu Leu Lys Asp Asp Tyr Ala Lys Phe Glu Leu Arg Asp Thr Asp Ala
            20                  25                  30

Ser Ile Ala Asn Ala Leu Arg Arg Val Met Ile Ala Glu Val Pro Thr
        35                  40                  45

Val Ala Ile Asp Leu Val Glu Ile Glu Val Asn Ser Ser Val Leu Asn
    50                  55                  60

Asp Glu Phe Ile Ala His Arg Leu Gly Leu Ile Pro Leu Thr Ser Glu
65                  70                  75                  80

Arg Ala Met Ser Met Arg Phe Ser Arg Asp Cys Asp Ala Cys Asp Gly
                85                  90                  95

Asp Gly Gln Cys Glu Phe Cys Ser Val Glu Phe His Leu Arg Val Lys
            100                 105                 110

Cys Met Thr Asp Gln Thr Leu Asp Val Thr Ser Lys Asp Leu Tyr Ser
        115                 120                 125

Ser Asp Pro Thr Val Ser Pro Val Asp Phe Ser Asp Pro Ser Ala Thr
    130                 135                 140

Asp Ser Asp Asn Asn Arg Gly Ile Ile Ile Val Lys Leu Arg Arg Gly
145                 150                 155                 160

Gln Glu Leu Lys Leu Arg Ala Ile Ala Arg Lys Gly Ile Gly Lys Asp
                165                 170                 175

His Ala Lys Trp Ser Pro Ala Ala Thr Val Thr Phe Met Tyr Glu Pro
            180                 185                 190

Glu Ile His Ile Asn Glu Asp Leu Met Glu Thr Leu Thr Leu Glu Glu
        195                 200                 205

Lys Arg Glu Trp Val Asp Ser Ser Pro Thr Arg Val Phe Glu Ile Asp
    210                 215                 220

Pro Val
225

<210> SEQ ID NO 10
<211> LENGTH: 240
<212> TYPE: PRT
<213> ORGANISM: Triticum aestivum
<220> FEATURE:
<221> NAME/KEY: misc_feature
<222> LOCATION: (1)..(240)
<223> OTHER INFORMATION: Ceres CLONE ID no. 698259T
<220> FEATURE:
<221> NAME/KEY: misc_feature
<222> LOCATION: (1)..(240)
<223> OTHER INFORMATION: Truncated portion of Ceres CLONE ID no. 698259

<400> SEQUENCE: 10

Met Glu Arg Ser Ala Ala Gly Ala Ser Tyr Gln Arg Phe Pro Arg Val
1               5                   10                  15

Arg Ile Arg Glu Leu Lys Asp Glu Tyr Ala Lys Phe Glu Leu Lys Asp
            20                  25                  30

Thr Asp Ala Ser Met Ala Asn Ala Leu Arg Arg Val Met Ile Ala Glu
        35                  40                  45
```

-continued

Val Pro Thr Val Ala Ile Asp Leu Val Glu Ile Glu Ser Asn Ser Ser
 50                  55                  60

Val Leu Asn Asp Glu Phe Leu Ala His Arg Leu Gly Leu Ile Pro Leu
65                  70                  75                  80

Thr Ser Ser Ala Ala Met Ser Met Arg Phe Ser Arg Asp Cys Asp Ala
                85                  90                  95

Cys Asp Gly Asp Gly Ser Cys Glu Tyr Cys Ser Val Glu Phe His Leu
            100                 105                 110

Ala Ala Arg Ala Thr Asp Ser Gly Gln Thr Leu Glu Val Thr Ser Thr
        115                 120                 125

Lys Asp Leu Arg Ser Thr Asp Pro Lys Val Cys Pro Val Asp Gln Gln
130                 135                 140

Arg Glu Tyr Gln Gln Ala Leu Gly Asn Val Asp Ala Tyr Glu Pro Asp
145                 150                 155                 160

Ala Ala Gly Asp His Arg Gly Ile Leu Ile Val Lys Leu Arg Arg Gly
                165                 170                 175

Gln Glu Leu Arg Leu Arg Ala Ile Ala Arg Lys Gly Ile Gly Lys Asp
            180                 185                 190

His Ala Lys Trp Ser Pro Ala Ala Thr Val Thr Phe Met Tyr Glu Pro
        195                 200                 205

Asp Ile Arg Ile Asn Gln Glu Leu Met Glu Thr Leu Thr Leu Glu Glu
210                 215                 220

Lys Gln Ser Trp Val Glu Ser Pro Thr Lys Val Phe Asp Ile Asp
225                 230                 235                 240

<210> SEQ ID NO 11
<211> LENGTH: 238
<212> TYPE: PRT
<213> ORGANISM: Zea mays
<220> FEATURE:
<221> NAME/KEY: misc_feature
<222> LOCATION: (1)..(238)
<223> OTHER INFORMATION: Ceres CLONE ID no. 244359T
<220> FEATURE:
<221> NAME/KEY: misc_feature
<222> LOCATION: (1)..(238)
<223> OTHER INFORMATION: Truncated portion of Ceres CLONE ID no. 244359

<400> SEQUENCE: 11

Met Asp Arg Pro Ser Gly Thr Ser Tyr Gln Arg Phe Pro Arg Val Arg
1               5                   10                  15

Ile Arg Glu Leu Lys Asp Asp Tyr Ala Lys Phe Glu Leu Arg Asp Thr
            20                  25                  30

Asp Ala Ser Met Ala Asn Ala Leu Arg Arg Val Met Ile Ala Glu Val
        35                  40                  45

Pro Thr Val Ala Ile Asp Leu Val Glu Ile Glu Val Asn Ser Ser Val
    50                  55                  60

Leu Asn Asp Glu Phe Ile Ala His Arg Leu Gly Leu Ile Pro Leu Thr
65                  70                  75                  80

Ser Ala Ala Ala Met Gln Met Arg Phe Ser Arg Asp Cys Asp Ala Cys
                85                  90                  95

Asp Gly Asp Gly Ser Cys Glu Tyr Cys Ser Val Glu Phe His Leu Ser
            100                 105                 110

Val His Ala Thr Asp Ser Asp Gln Thr Leu Glu Val Thr Ser Asn Asp
        115                 120                 125

Leu Arg Ser Met Asp Pro Lys Val Cys Pro Val Asp Gln Ala Arg Ala
130                 135                 140

```
Tyr Gln His Ala Leu Gly Gly Thr Asp Pro Phe Ala Asn Ala Ser
145                 150                 155                 160

Asn Glu Asn Arg Gly Ile Leu Ile Val Lys Leu Arg Arg Gly Gln Glu
            165                 170                 175

Leu Arg Leu Arg Ala Ile Ala Arg Lys Gly Ile Gly Lys Asp His Ala
        180                 185                 190

Lys Trp Ser Pro Ala Ala Thr Val Thr Phe Met Tyr Glu Pro Asp Ile
        195                 200                 205

Arg Ile Asn Glu Glu Leu Met Glu Thr Leu Thr Val Glu Glu Arg Ile
        210                 215                 220

Ser Leu Ile Glu Ser Ser Pro Thr Lys Val Phe Glu Leu Asp
225                 230                 235
```

```
<210> SEQ ID NO 12
<211> LENGTH: 239
<212> TYPE: PRT
<213> ORGANISM: Zea mays
<220> FEATURE:
<221> NAME/KEY: misc_feature
<222> LOCATION: (1)..(239)
<223> OTHER INFORMATION: Public GI no. 50898416T
<220> FEATURE:
<221> NAME/KEY: misc_feature
<222> LOCATION: (1)..(239)
<223> OTHER INFORMATION: Truncated portion of Public GI no. 50898416

<400> SEQUENCE: 12

Met Glu Arg Ala Ala Gly Gly Val Ser Tyr Gln Arg Phe Pro Arg Val
1               5                   10                  15

Arg Ile Arg Glu Leu Lys Asp Asp Tyr Ala Lys Phe Glu Leu Arg Asp
            20                  25                  30

Thr Asp Ala Ser Met Ala Asn Ala Leu Arg Arg Val Met Ile Ala Glu
        35                  40                  45

Val Pro Thr Val Ala Ile Asp Leu Val Glu Ile Glu Val Asn Ser Ser
    50                  55                  60

Val Leu Asn Asp Glu Phe Ile Ala His Arg Leu Gly Leu Ile Pro Leu
65                  70                  75                  80

Thr Ser Ala Ala Ala Met Ala Met Arg Phe Ser Arg Asp Cys Asp Ala
                85                  90                  95

Cys Asp Gly Asp Gly Ser Cys Glu Tyr Cys Ser Val Glu Phe His Leu
            100                 105                 110

Ala Ala Arg Ala Thr Asp Ser Asp Gln Thr Leu Glu Val Thr Ser Asn
        115                 120                 125

Asp Leu Arg Ser Thr Asp Pro Lys Val Cys Pro Val Asp Gln Ala Arg
    130                 135                 140

Ala Tyr Gln His Ala Leu Gly Gly Thr Glu Pro Phe Asp Thr Ala Ala
145                 150                 155                 160

Ala Ala Asp Gln Arg Gly Ile Leu Ile Val Lys Leu Arg Arg Gly Gln
                165                 170                 175

Glu Leu Arg Leu Arg Ala Ile Ala Arg Lys Gly Ile Gly Lys Asp His
            180                 185                 190

Ala Lys Trp Ser Pro Ala Ala Thr Val Thr Phe Met Tyr Glu Pro Glu
        195                 200                 205

Ile Arg Ile Asn Glu Glu Leu Met Glu Thr Leu Thr Leu Glu Glu Lys
    210                 215                 220

Arg Asn Leu Val Glu Ser Ser Pro Thr Lys Val Phe Asn Ile Asp
225                 230                 235
```

```
<210> SEQ ID NO 13
<211> LENGTH: 725
<212> TYPE: DNA
<213> ORGANISM: Glycine max
<220> FEATURE:
<221> NAME/KEY: misc_feature
<222> LOCATION: (1)..(725)
<223> OTHER INFORMATION: Ceres CLONE ID no. 625627
<220> FEATURE:
<221> NAME/KEY: CDS
<222> LOCATION: (39)..(561)
<223> OTHER INFORMATION: Referenced by SEQ ID NO: 14
<220> FEATURE:
<221> NAME/KEY: misc_feature
<222> LOCATION: (1)..(725)
<223> OTHER INFORMATION: Chimeric DNA

<400> SEQUENCE: 13
aatataacca cctcacattt ttttcatcac tccttaaaga tgacaacagc agaaaaaact    60
tcaaacttgg atctcatacg ccaacacctc tttggtgaaa acatcatctc agactcctcc   120
tcctttgtct ccaatctcca tcatcatcct gtgaaacttg aaccccctc atcaccagaa    180 tttgatttca cctcatatat cttagataac aacacaagca gcaacttctt cacattcctt   240
gaaggctatg atttggtggc agacatgaag tttgtaattg attcagacaa caccaccacc   300
atggtgatcc cttcaaagga ggttataaag aaatgcaata ttaattctcc tgaagaacaa   360
ccaatggtgt catcatcatc agaagagaag ccaacaatga aaaagtcaga acattatgat   420
gaggcaaagc gttataggg agtaggaga aggccatggg ggaaatttgc tgctgaaatc     480
cgtgacccta caaggaaagg acaagggtt actagaagat cttcgtcgtc caatgcttcc   540
ttgcccgcaa gcccattgcg ataattagtt acagcattgg aaaagaataa gcaatgttct   600
cgattgcact tcattccctt tcaaaagaag gcaatttggg ggcaagcttc ttttttgttc    660
atagccgaat tagtcacaac atttattcat ggatgcaac attgggactc ttggaaagtg    720
ttggc                                                               725

<210> SEQ ID NO 14
<211> LENGTH: 174
<212> TYPE: PRT
<213> ORGANISM: Glycine max
<220> FEATURE:
<221> NAME/KEY: misc_feature
<222> LOCATION: (1)..(174)
<223> OTHER INFORMATION: Chimeric Polypeptide
<220> FEATURE:
<221> NAME/KEY: misc_feature
<222> LOCATION: (130)..(174)
<223> OTHER INFORMATION: Pfam Name: AP2; Pfam Description: AP2 domain

<400> SEQUENCE: 14

Met Thr Thr Ala Glu Lys Thr Ser Asn Leu Asp Leu Ile Arg Gln His
1               5                  10                  15

Leu Phe Gly Glu Asn Ile Ile Ser Asp Ser Ser Ser Phe Val Ser Asn
                20                  25                  30

Leu His His His Pro Val Lys Leu Glu Pro Pro Ser Pro Glu Phe
        35                  40                  45

Asp Phe Thr Ser Tyr Ile Leu Asp Asn Asn Thr Ser Ser Asn Phe Phe
    50                  55                  60

Thr Phe Leu Glu Gly Tyr Asp Leu Val Ala Asp Met Lys Phe Val Ile
65                  70                  75                  80

Asp Ser Asp Asn Thr Thr Thr Met Val Ile Pro Ser Lys Glu Val Ile
                85                  90                  95

Lys Lys Cys Asn Ile Asn Ser Pro Glu Glu Gln Pro Met Val Ser Ser
```

-continued

```
                100                 105                 110
Ser Ser Glu Glu Lys Pro Thr Met Lys Lys Ser Glu His Tyr Asp Glu
        115                 120                 125

Ala Lys Arg Tyr Arg Gly Val Arg Arg Arg Pro Trp Gly Lys Phe Ala
        130                 135                 140

Ala Glu Ile Arg Asp Pro Thr Arg Lys Gly Thr Arg Val Thr Arg Arg
145                 150                 155                 160

Ser Ser Ser Ser Asn Ala Ser Leu Pro Ala Ser Pro Leu Arg
                165                 170
```